United States Patent
Wuhrer et al.

(10) Patent No.: US 10,151,759 B2
(45) Date of Patent: Dec. 11, 2018

(54) METHOD FOR THE PURIFICATION OF A GLYCAN AND/OR A GLYCOCONJUGATE BY CHROMATOGRAPHY USING A STATIONARY PHASE COMPRISING COTTON

(75) Inventors: Manfred Wuhrer, Leiden (NL); Mahdi Hemayatkar, Leiden (NL); Maurice Henricus Johannes Selman, Leiden (NL)

(73) Assignee: Hoffmann-La Roche Inc., Little Falls, NJ (US)

(*) Notice: Subject to any disclaimer, the term of this patent is extended or adjusted under 35 U.S.C. 154(b) by 0 days.

(21) Appl. No.: 13/984,384

(22) PCT Filed: Feb. 10, 2012

(86) PCT No.: PCT/EP2012/052335
§ 371 (c)(1),
(2), (4) Date: Aug. 8, 2013

(87) PCT Pub. No.: WO2012/107572
PCT Pub. Date: Aug. 16, 2012

(65) Prior Publication Data
US 2013/0316463 A1  Nov. 28, 2013

(30) Foreign Application Priority Data
Feb. 10, 2011  (EP) .................. 11250152

(51) Int. Cl.
*G01N 33/68* (2006.01)
*C07K 1/22* (2006.01)
(Continued)

(52) U.S. Cl.
CPC ......... *G01N 33/6851* (2013.01); *B01D 15/26* (2013.01); *B01D 15/305* (2013.01);
(Continued)

(58) Field of Classification Search
CPC ........ B01D 15/305; B01D 15/26; C07K 1/20; C07K 1/22; G01N 33/6848; G01N 33/6851; Y10T 436/143333; C07H 1/06
(Continued)

(56) References Cited

U.S. PATENT DOCUMENTS 4,384,957 A * 5/1983 Crowder, III .......... B01D 15/22
  210/198.2
5,338,834 A * 8/1994 Williams ........... C07K 14/5412
  530/351
(Continued)

FOREIGN PATENT DOCUMENTS

EP  1106723 A1  7/1999
JP  61118661 A  6/1986
(Continued)

OTHER PUBLICATIONS

Yang et al. Liquid Chromatography Using Cellulosic Continuous Stationary Phase(1993). Liquid Chromatography. pp. 147-160.*
(Continued)

*Primary Examiner* — Rebecca M Fritchman
(74) *Attorney, Agent, or Firm* — Shumaker & Sieffert, P.A.

(57) ABSTRACT

A method of purifying a glycan and/or a glycoconjugate comprising the steps of: (a) providing a stationary phase that comprises cotton; (b) applying a glycan and/or glycoconjugate-containing sample to the stationary phase; (c) washing the stationary phase with a first solvent; and (d) eluting the glycan and/or glycoconjugate from the stationary phase with a second solvent. A kit for purifying a glycan and/or glycoconjugate, the kit comprising: a stationary phase comprising cotton; and instructions for purifying a glycan and/or glycoconjugate according to the disclosed method.

20 Claims, 28 Drawing Sheets

(51) Int. Cl.
*B01D 15/30* (2006.01)
*C07K 1/20* (2006.01)
*B01D 15/26* (2006.01)
*C07H 1/06* (2006.01)

(52) U.S. Cl.
CPC ............... *C07H 1/06* (2013.01); *C07K 1/20* (2013.01); *C07K 1/22* (2013.01); *G01N 33/6848* (2013.01); *Y10T 436/143333* (2015.01)

(58) Field of Classification Search
USPC .......................................................... 436/87
See application file for complete search history.

(56) References Cited

U.S. PATENT DOCUMENTS

| 6,887,486 B2 | 5/2005 | Gregoire |
| 2009/0275472 A1* | 11/2009 | Pretorius .................. 504/116.1 |

FOREIGN PATENT DOCUMENTS

| JP | 2002519303 A | 7/2002 |
| JP | 2005031041 A | 2/2005 |
| WO | 99/62939 A1 | 6/1999 |
| WO | 2012107572 A1 | 8/2012 |

OTHER PUBLICATIONS

Merriam Webster Dictionary(Pages attached).*
International Search Report and Written Opinion for international patent application No. PCT/EP2012/052335, dated Apr. 18, 2012, 13 pages.
Snovida et al., "A simple cellulose column procedure for selective enrichment of glycopeptides and characterization by nan LC coupled dwith electron-transfer and high-energy collisional-dissociation tandem mass spectrometry," Carbohydrate Research, vol. 345, No. 6, Apr. 19, 2010, pp. 792-801.
Wada et al., "Hydrophilic Affinity Isolation and MALDI Multiple-Stage Tandem Mass Spectrometry of Glycopeptides for Glycoproteomics," Analytical Chemistry, vol. 76, No. 22, Nov. 1, 2004, pp. 6560-6565.
Ruhaak et al.,"Hydrophilic Interaction Chromatography-Based High-Throughput Sample Preparation Method for N-Glycan Analysis from Total Human Plasma Glycoproteins," Analytical Chemistry, vol. 80, No. 15, Aug. 1, 2008, pp. 6119-6126.
Luo et al.,"Hydrophilic interaction 10μ m I.D. porous open tubular columns for ultratrace glycan analysis by liquid chromatography-mass spectrometry," Journal of Chromatography, vol. 1216, Feb. 20, 2009, pp. 1223-1231.
"Cellulose Processing", NOSB TAP review Compiled by OMRI, Sep. 28, 2001, 17 pp.
Selman, et al., "Immunoglobulin G Glycopeptide Profiling by Matrix-Assisted Laser Desorption Ionization Fourier Transform Ion Cyclotron Resonance Mass Spectrometry," Department of Biochemistry and Molecular Biology, Anal. Chem., vol. 82, No. 3, Feb. 1, 2010, pp. 1073-1081.
Mechref, et al., "Structural Investigations of Glycoconjugates at High Sensitivity," Department of Chemistry, Jan. 29, 2002, 42 pp.
Mysling, et al., "Utilizing Ion-Pairing Hydrophilic Interaction Chriomatography Solid Phase Extraction for Efficient Glycopeptide Enrichment in Glycoproteomics," Department of Biochemistry and Molecular Biology, Anal. Chem., Jul. 1, 2010, pp. 5598-5609.
Wuhrer, et al., "Structural Glycomics Using Hyrdophilic Interaction Chromatography (HILIC) with Mass Spectrometry," Mass Spectrometry Reviews, Jun. 15, 2007, pp. 192-206.
Ruhaak, et al., "Glycan labeling strategies and their use in identification and quantification," Anal Bioanal Chem, 397, Jan. 22, 2010, pp. 3457-3481.
Wuhrer, et al. "Glycosylation profiling of Immunoglobulin G (IgG) subclasses from human serum," Proteomics, Nov. 2007, pp. 4070-4081.
Craft, et al. "Microcolumn capture and design of proteins combined with mass spectrometry for protein identification," J. Proteome Res., 2002, vol. 1, pp. 537-547.
Fan, "Chemical Testing of Textiles," The Textile Institute, Sep. 2005, 337 pp.
European Patent Application No. 11250152.3, by Whurer et al., filed Feb. 10, 2011.
Shimizu, et al., "Rapid and simple preperation of N-linked oligosaccharides by cellulose-column chromatography," Elsevier, Carboyhdrate Research 332, Feb. 2001, pp. 381-388.
Yang, et al., "Liquid Chromatography Using Cellulosic Continuous Stationary Phases," Advances in Biochemical Engineering Biotechnology, 1993, accessed on Jun. 23, 2015, pp. 147-160.
Yodoshi, et al., "Development of Methods for the Specific Enrichment of Glycopeptides for the LC/MS Analysis," Chromatography, vol. 30, No. 2, 2009, retrieved on Aug. 7, 2015, pp. 61-67 [translation of abstract only].
"Bond Elut Cellulose," Solid Phase Extraction (SPE), Agilent Technologies, retrieved on Aug. 7, 2015 from <http://www.chem.agilent.com/en-US/products-services/Columns-Sample-Preparation/Sample-Preparation/Solid-Phase-Extraction-(SPE)/Bond-Elut-Cellulose/Pages/default.aspx>, 5 pp.

* cited by examiner

* potassium adducts

* potassium adducts

* sodium adduct      ¥ potassium adduct

METHOD FOR THE PURIFICATION OF A GLYCAN AND/OR A GLYCOCONJUGATE BY CHROMATOGRAPHY USING A STATIONARY PHASE COMPRISING COTTON

CROSS REFERENCE TO RELATED APPLICATIONS

This application is a U.S. National Stage Application of International Application No. PCT/EP2012/052335, filed Feb. 10, 2012, which claims the benefit of European Application 11250152.3, filed Feb. 10, 2011. The entire content of each of these applications is incorporated herein by reference.

The present invention relates to a purification method. In particular, the present invention relates to a method for purifying a glycan or a glycoconjugate.

Due to its speed, resolution and sensitivity, modern mass spectrometry provides great opportunities for detailed structural characterization of protein glycosylation including protein identification, determination of site-specific glycosylation profiles, and structural characterization of glycans at the level of glycopeptides or released glycans.

For the efficient ionization and detection of glycopeptides and glycans, enrichment or purification steps are often required. Hydrophilic interaction liquid chromatography (HILIC) has been found to be particularly suitable for this purpose, next to graphitized carbon solid phase extraction (SPE), hydrazine coupling, and lectin or antibody affinity chromatography (as described in Mechref et al., *Chem. Rev.* 2002, 102, 321-369).

While the specificity of lectins and antibodies often only allows the isolation of a subset of glycans or glycopeptides from a pool, HILIC and graphitized carbon SPE can be employed for isolation of a broad range of glycoconjugates, making these adsorption chromatography methods applicable in a wide range of glycomics and glycoproteomics studies.

HILIC SPE has been found to be particularly useful for the enrichment of tryptic N-glycopeptides. For this purpose, ZIC-HILIC stationary phases have been applied in ion-pairing mode using trifluoroacetic acid as a mobile phase additive (as described in Mysling et al *Anal. Chem.* 2010, 82, 5598-5609).

Alternatively, carbohydrate-based stationary phases such as Sepharose and microcrystalline cellulose have been applied for N-glycopeptide isolation (as described in Wada, Y et al.; *Anal. Chem.* 2004, 76, 6560-6565).

An important feature of these carbohydrate-based stationary phases is that they are non-ionic. HILIC adsorption is, therefore, dominated by hydrogen bonding of the glycan moieties with the stationary phase, while non-glycosylated peptides, lipids, salts and detergents tend to show low or no retention (as described in Wuhrer et al., *Mass Spectrom. Rev.* 2009, 28, 192-206).

Retention of glycoconjugates is usually achieved with acetonitrile concentrations in the range of 80%, while elution is performed with high water content. The required elution conditions make HILIC very compatible with mass spectrometry, both in online and off-line mode.

It is known that IgG Fc N-glycosylation profiles can be analyzed in a reproducible and robust manner by MALDI-MS after HILIC SPE with Sepharose as well as microcrystalline cellulose performed in batch mode or 96-well plate high-throughput format (Selman et al.; *Anal. Chem.* 2010, 82, 1073-1081).

There remains a need for efficient and effective methods for the purification of molecules such as glycans and glycoconjugates.

It has been found by the present applicant that cotton wool can be used to prepare devices which allow simple and fast purification of molecules such as glycoconjugates and glycans. The present invention allows for the use of cotton wool microtips as a key part of simple, fast and robust purification procedures, such as for IgG Fc N-glycosylation profiling and for the successful removal of detergents and salts when extracting N-glycans after N-glycosidase F (PNGase F) treatment of glycoproteins.

According to the invention, there is provided a method of purifying a glycan and/or a glycoconjugate comprising the steps of:
(a) providing a stationary phase that comprises cotton;
(b) applying a glycan and/or glycoconjugate-containing sample to the stationary phase;
(c) washing the stationary phase with a first solvent; and
(d) eluting the glycan and/or glycoconjugate from the stationary phase with a second solvent.

Preferably, in step (b) the glycan and/or glycoconjugate-containing sample comprises an organic solvent; wherein the organic solvent comprises acetonitrile, methanol, ethanol, propanol, isopropanol, butanol, or tetrahydrofuran.

Preferably, the organic solvent is between 70% and 88% v/v acetonitrile in water; more preferably wherein the organic solvent is between 75% and 85% v/v acetonitrile in water; more preferably wherein the organic solvent is 83% v/v acetonitrile in water.

Preferably, in step (c) the first solvent is a solvent mixture comprising water, an organic solvent and an acid. More preferably, the organic solvent is acetonitrile, methanol, ethanol, propanol, isopropanol, butanol or tetrahydrofuran and the acid is trifluoroacetic acid, formic acid, acetic acid, pentafluoropropionic acid, or heptafluorobutyric acid.

Conveniently, the above solvent mixture comprises between 75% and 90% v/v organic solvent and between 0.1% and 1% v/v acid in water. Alternatively, the solvent mixture comprises between 70% and 95% v/v organic solvent and between 0.1% and 3% v/v acid in water. Preferably, the solvent mixture comprises 83% v/v acetonitrile and 0.1% v/v trifluoroacetic acid in water.

Preferably, in step (d) the second solvent comprises a polar solvent. More preferably, the polar solvent is water, dimethylsulfoxide, or dimethylformamide.

Optionally, the second solvent comprises more polar solvent than the first solvent.

Preferably, in step (c) washing removes salts, non-glycosylated peptides, lipids, detergents, excess reducing-end label, reducing agents, denaturants and denatured proteins from the stationary phase.

Optionally, the glycoconjugate is a glycoprotein, glycopeptide or glycolipid. Preferably, the method is for purification of a glycan or a glycopeptide.

Conveniently, the glycopeptide is an IgG glycopeptide.
Preferably, the IgG glycopeptide is a tryptic IgG Fc N-glycopeptide.

Optionally, the glycan is an N-glycan.
Conveniently, the stationary phase is re-usable.
Preferably, the stationary phase comprises cotton wool.
Optionally, the stationary phase consists of cotton wool.
Conveniently, the stationary phase contains about 500 µg of cotton wool. The stationary phase could contain from about 250 to 750 µg of cotton wool.

Preferably, the method further comprises the step of performing mass spectrometric analysis or fluorescence detection on the eluted glycan and/or glycoconjugate.

Optionally, the mass spectrometric analysis is MALDI-TOF MS detection.

Preferably, glycans labelled by reductive amination with a fluorescent dye are analysed by HPLC with fluorescence detection, or capillary gel electrophoresis with laser-induced fluorescence detection (CGE-LIF).

Conveniently, the method further comprises the step of glycosylation profiling at the glycopeptide level of the eluted glycopeptides.

Preferably, the stationary phase is held in an open ended vessel. The vessel may be open at one end, or at both ends. Preferably the vessel is open at both ends.

Optionally, the open-ended vessel is a pipette, a multi-channel pipette or a pipette tip.

Conveniently, the purification step can be used to extract glycans after PNGase F treatment of glycoproteins, extract glycans after fluorescent labelling by reductive amination, or enrich N-glycopeptides from proteolytic digests.

According to a further aspect of the invention, there is provided a kit for purifying a glycan and/or glycoconjugate, the kit comprising a stationary phase comprising cotton and instructions for purifying a glycan and/or glycoconjugate according to the method of the invention. The kit may further comprise a vessel for holding the stationary phase. Preferably, the kit comprises a stationary phase located in an open-ended vessel.

Optionally, the kit comprises a pipette tip holding a cotton stationary phase.

The present invention will now be described, by way of example, with reference to the accompanying figures, in which:

FIG. 1 comprises four photographs showing the preparation of a cotton HILIC SPE microtip. From a cotton wool pad (A), approximately 500 μg is taken (B) and pushed into a 10 μl pipette tip using a blunt metal needle (C). The cotton is pushed down into the end part of the tip (D);

FIG. 2 shows two MALDI-TOF-mass spectrometric profiles of IgG glycopeptides prepared using cotton HILIC SPE microtips. Mass spectra were registered in positive reflectron-mode using CHCA matrix (A) and in positive linear-mode using DHB matrix (B). IgG1 and IgG2 glycopeptides are represented by continued and dashed arrows, respectively: square, N-acetylglucosamine; triangle, fucose; dark circle, mannose; light circle, galactose; diamond, N-acetyl-neuraminic acid; pep, peptide moiety;

FIG. 3 shows IgG1 Fc N-glycosylation profiling registered by MALDI-TOF-MS Repeatability of IgG1 glycopeptide profiling applying cotton HILIC SPE microtips. IgG1 glycopeptides were detected by MALDI-TOF-MS in reflectron-mode using CHCA matrix (A, C) and in linear-mode using DHB matrix (B, D). Samples were prepared after digestion using the neutralization method followed by desalting with cotton HILIC SPE microtips prepared from three different brands of cotton wool pads (A, B). The resulting profiles were compared with the pattern of glycoforms purified by Sepharose beads or cotton HILIC SPE microtips after drying by vacuum centrifugation, and digestion with sequencing grade trypsin (C, D). For each independent experiment, relative intensities and RSDs were calculated from 8 replicates;

FIG. 4 shows repeatability of cotton HILIC SPE microtips for desalting and purification of IgG glycopeptides. Analysis was performed by reflectron-mode MALDI-TOF-MS with CHCA matrix. A tryptic IgG digest pool was desalted 8 times either with one cotton HILIC microtip (A and B) or with eight different cotton HILIC microtips (C and D). The experiment was repeated on four different days;

FIG. 5 shows repeatability of IgG2 glycopeptide profiling applying cotton HILIC SPE microtips. IgG2 glycopeptides were detected by MALDI-TOF-MS in reflectron-mode using CHCA matrix (A, C) and in linear-mode using DHB matrix (B, D). Samples were prepared after digestion using the neutralization method followed by desalting with cotton HILIC SPE microtips prepared from three different brands of cotton wool pads (A, B). The resulting profiles were compared with the pattern of glycoforms purified by Sepharose beads or cotton HILIC SPE microtips after drying by vacuum centrifugation, and digestion with sequencing grade trypsin (C, D). For each independent experiment, relative intensities and RSDs were calculated from 8 replicates.

Figure 11A:
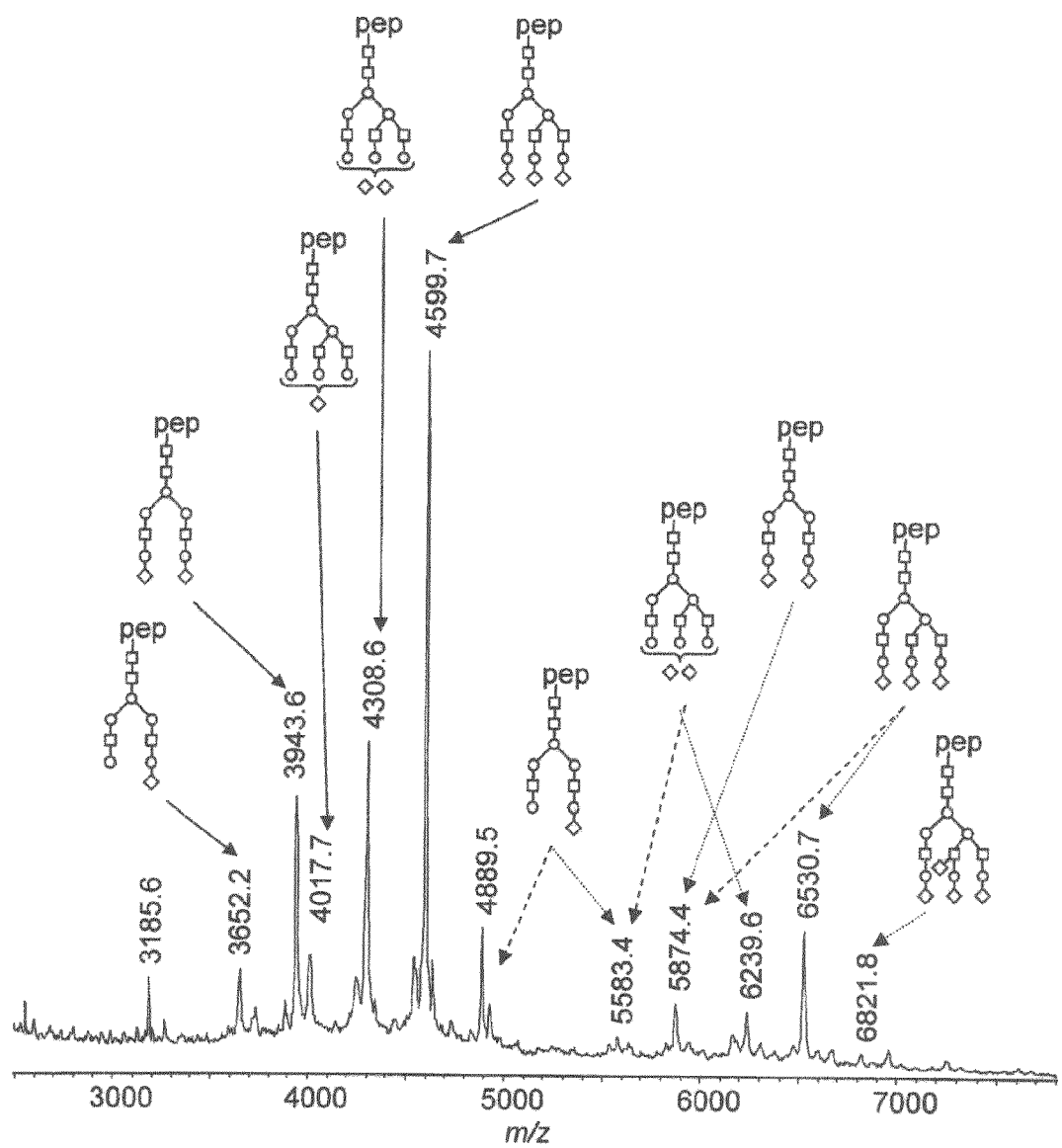
Figure 11B:
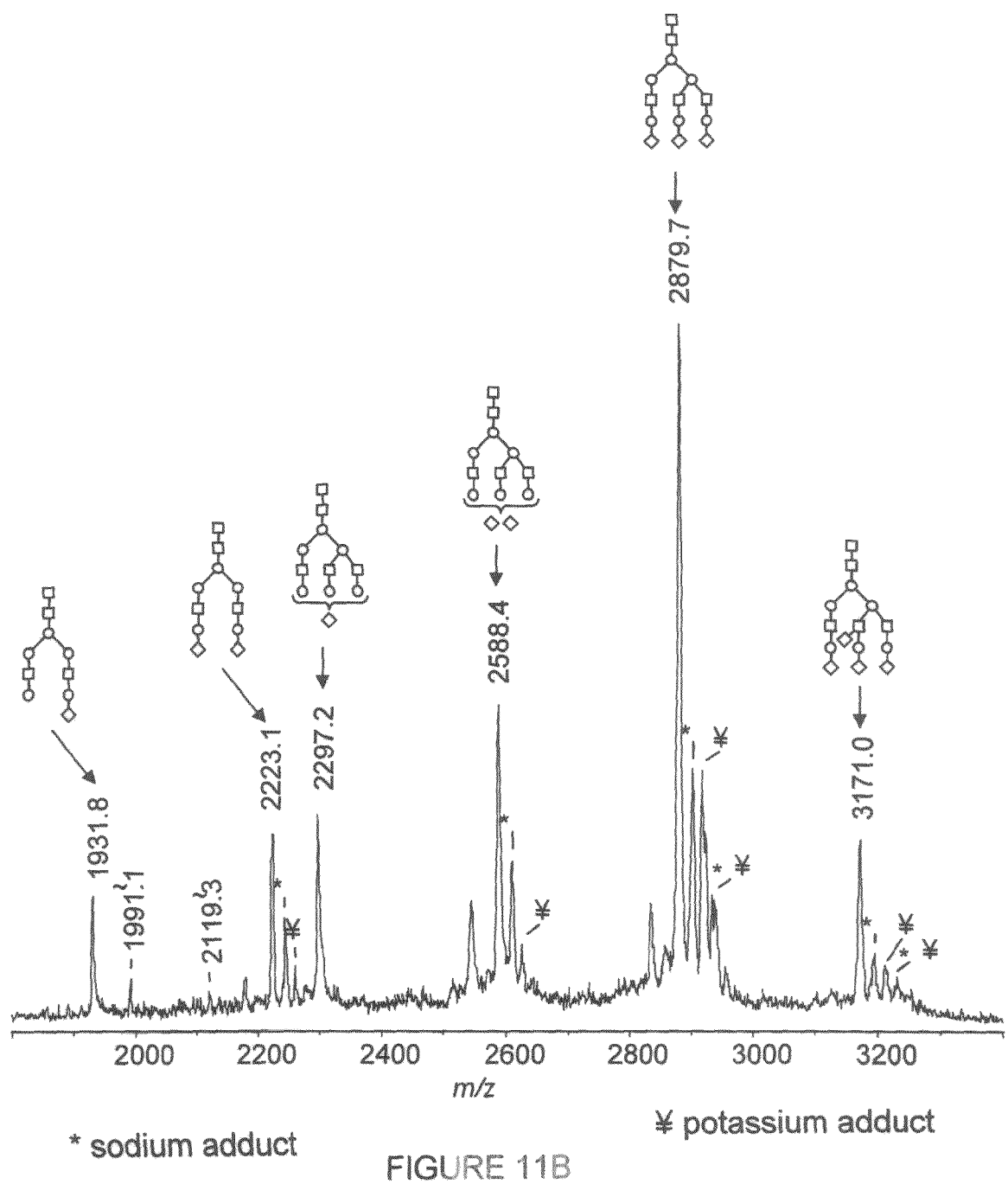
Figure 12A:
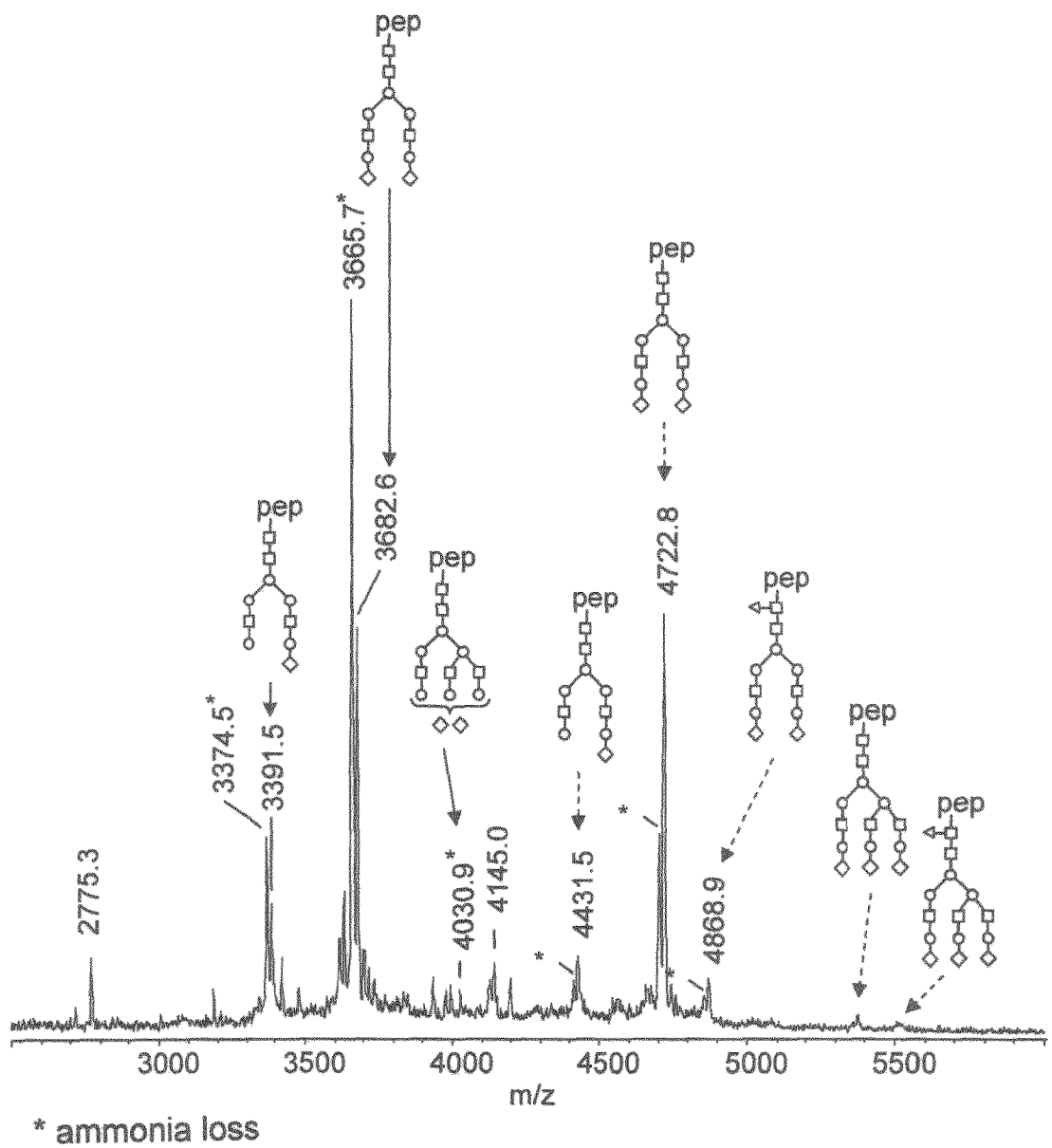
Figure 12B:
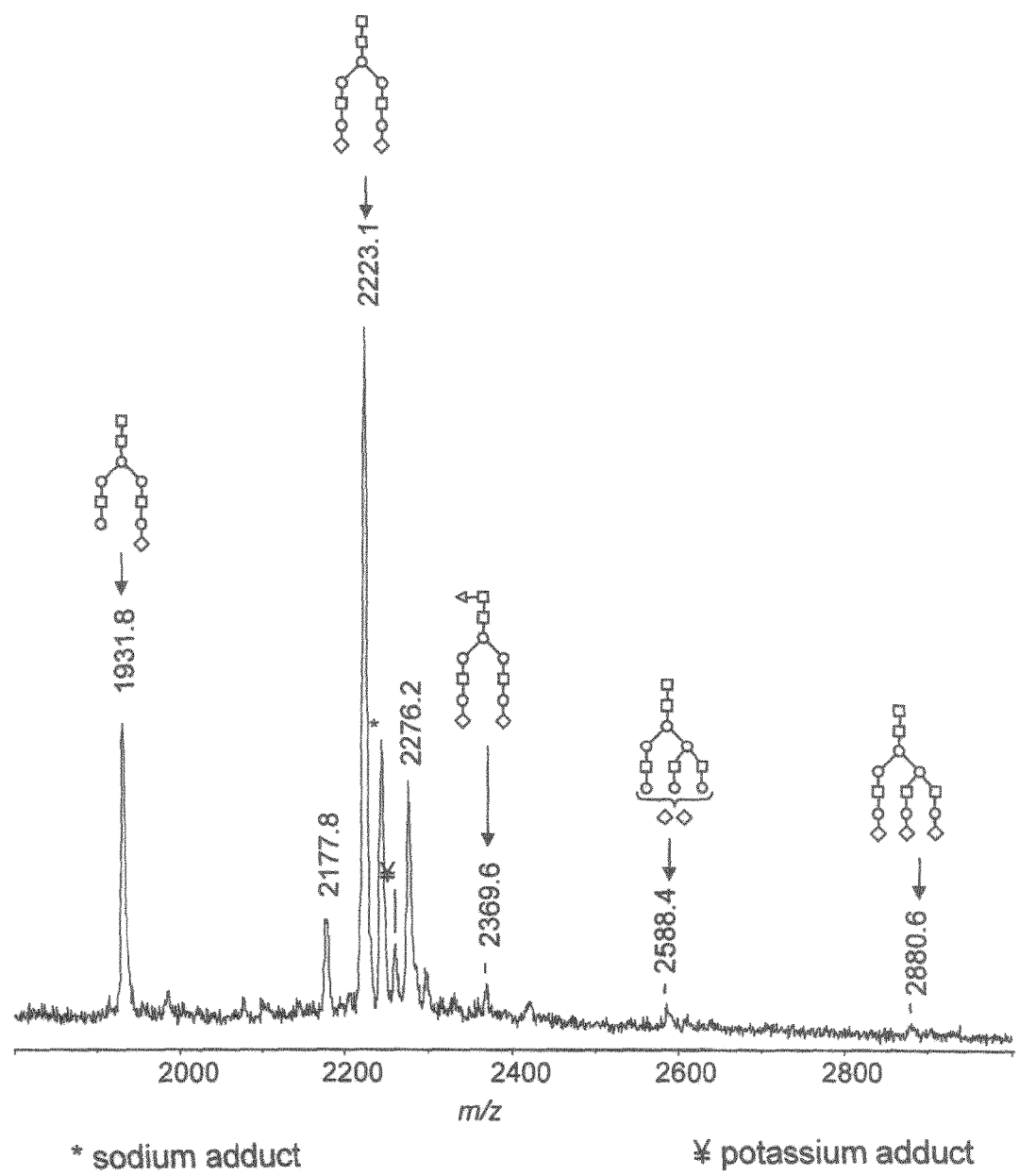

FIG. 11 shows linear-negative ion mode MALDI-TOF-MS spectra of tryptic glycopeptides (A) and PNGase F released N-glycans (B) from bovine fetuin, after purification using cotton HILIC SPE microtips; and FIG. 12 shows linear-negative ion mode MALDI-TOF-MS spectra of tryptic glycopeptides (A) and PNGase F released N-glycans (B) from human apo-transferrin glycopeptides, after purification using cotton HILIC SPE microtips.

According to the present invention there is provided a cotton wool HILIC SPE microtip procedure for the extraction of glycoconjugates and/or glycans. A glycoconjugate is a moiety comprising a carbohydrate covalently linked to another moiety. Glycoconjugates include glycoproteins, glycopeptides, peptidoglycans, glycolipids and lipopolysaccharides. Preferred glycoconjugates are glycoproteins, glycopeptides and peptidoglycans. Preferably the glycoconjugate is a glycopeptide. Preferably the glycoconjugate is a glycoprotein.

This procedure shows good repeatability and does not appear to depend on a specific brand or batch of cotton wool pads. The cotton wool microtips are cheap and can be easily and quickly prepared in a lab.

Microtips have been introduced with various stationary phases including ZIC-HILIC microtips. In contrast to some other microtips, the cotton stationary phase stays in position, both with liquid aspiration and dispension. Moreover, the stationary phase appeared to be compatible with acidic and high acetonitrile conditions (as described in Craft et al., *J. Proteome Res.* 2002, 1, 537-547).

Next to establishing the HILIC SPE microtips, two additional modifications were introduced to an IgG Fc N-glycosylation profiling protocol (previously described in Craft, et al *J. Proteome Res.* 2002, 1, 537-547). First, tryptic cleavage was performed using TPCK-treated trypsin instead of the more expensive sequencing-grade trypsin. Second, the rather laborious vacuum centrifugation step, which was applied to remove formic acid from the Protein A eluates, has been substituted by a simple neutralization, making the protocol easier and more suitable for automation.

Raw cotton is mainly composed of cellulose (over 90%) (Fan Qinguo, Editor, 2005, Chemical testing of textiles, 336pp; Woodhead Publishing ISBN: 1855739178). Cotton is used in a variety of commercial products such as clothing, cotton swabs (q-tips) and cotton wool pads. For the manufacturing of cotton wool for pads and q-tips, the raw cotton is subjected to extensive bleaching after which the fibers are carded, randomized and treated with water at high pressure to cross and tie the fibers. During the manufacturing process traces of wax and protein are removed from cotton, and as a result cotton wool pads are composed of virtually pure cellulose.

Similar to Poly HEA and carbohydrate HILIC stationary phases such as Sepharose and microcrystalline cellulose, cotton wool is a non-ionic, neutral stationary phase, and HILIC retention is expected to be caused solely by hydrogen bonding. By contrast, ionic interactions may contribute to HILIC retention in ZIC-HILIC as well as with amine-based stationary phases, which may be modulated by the addition of salt and/or ion-pairing reagents (as described in Wuhrer et al., *Mass Spectrom. Rev.* 2009, 28, 192-206). Sepharose and microcrystalline cellulose have been successfully applied for reproducible IgG Fc N-glycosylation profiling, and cotton wool HILIC microtips may be used for the same purpose, with the specific advantage of their ease of use, their suitability for minute amounts of samples, and the possibility of directly eluting samples onto the MALDI target plate.

Notably, the present inventors have found that cotton wool HILIC microtips are not only suitable for removal of salts and most non-glycosylated peptides, but also for the removal of detergents such as SDS from tryptic digests. Therefore, cotton wool microtips may serve as sample clean-up devices in glycomics and proteomics applications in which denaturants and surfactants are often added to improve protein solubility and proteolytic cleavage.

Carbohydrate-based stationary HILIC phases can additionally be used for total plasma N-glycome analysis by mass spectrometry (as described in Ruhaak et al., *Anal. Bioanal. Chem.* 2010, 397, 3457-3481). AA-labeled N-glycans are purified from the labeling mix which contains excess label, reducing agent, various salts, plasma lipids, and large amounts of detergents together with denatured proteins, followed by glycan detection using MS. Cotton wool microtips are likewise suitable for removal of salts and detergents after enzymatic N-glycan release which, together with the favorable SPE elution conditions, resulted in efficient mass spectrometric detection of N-glycans (FIGS. 6, 7 8 and 9).

The cotton wool microtips of the present invention are convenient devices for simple and fast sample preparation of tryptic IgG digests, and allow the determination of IgG Fc N-glycosylation features such as galactosylation, sialylation, fucosylation, and incidence of bisecting N-acetylglucosamine by MALDI-MS analysis.

The biological activity of IgG is modulated by the Fc N-glycosylation, which influences both antibody-dependent cellular cytotoxicity and complement-dependent cytotoxicity. Hence, IgG Fc N-glycosylation of biotechnologically produced IgGs is being designed in order to maximize the efficacy in e.g. anti-cancer therapy (next generation therapeutic antibodies).

Cotton wool HILIC microtips are particularly convenient tools for the preparation of low amounts of samples for mass spectrometric analysis and may be applied in (1) IgG Fc N-glycosylation profiling of clinical samples which often show disease-associated IgG glycosylation changes, and (2) analysis of recombinantly expressed IgG.

Similar to other HILIC stationary phases, cotton wool microtips are also useful in other typical HILIC SPE applications such as the enrichment of N-glycopeptides from complex proteolytic digests, the extraction of N-glycans after PNGase F treatment of glycoproteins or glycopeptides, or the clean-up of glycans after fluorescent labeling by reductive amination. The cotton wool tips are prepared by hand. As such a tip to tip capacity variation has to be taken into account. The capacity requirement varies with the sample and can easily be established for the user's own application.

While cotton wool HILIC microtips are a good choice for processing low numbers of samples, they are also applicable to larger numbers of samples by using multi-channel pipettes or by transferring the SPE method to a robotic platform.

EXPERIMENTAL

IgG Purification

Polyclonal human IgGs were purified from plasma by affinity chromatography with immobilized protein (according to the technique disclosed in Wuhrer et al., Proteomics 2007, 7, 4070-4081 with minor modifications).

rProtein A-Sepharose™ beads (GE Healthcare, Eindhoven, The Netherlands) were washed three times with phosphate buffer saline (PBS). To each well of a 96-well OF1100 filter plate (Orochem Technologies Inc., Lombard, Ill.) 50 µl PBS, 50 µl of slurry containing approximately 5 µl of beads and 2 µl of human plasma were applied. The plate was covered with a cap and incubated at room temperature with gentle agitation for 1 hour.

After incubation, beads were washed with 3×200 µl PBS and 3×200 µl of water on a vacuum manifold. Captured human polyclonal IgGs were released from protein A and eluted into a polypropylene 96-well V-bottom plate (V96 microwell; NUNC, Roskilde, Denmark) by 5 minutes incubation with 40 µl of 100 mM formic acid (Fluka, Steinheim, Germany) and centrifugation (1 min at 18 g), respectively. After centrifugation, the eluates were neutralized (final pH >7) with 20 µl of 300 mM ammonium bicarbonate. Alternatively, the eluates were dried by vacuum centrifugation for 2 hours.

Trypsin Digestion

Tosyl phenylalanyl chloromethyl ketone (TPCK) treated trypsin (Sigma-Aldrich, Steinheim, Germany) was dissolved in ice-cold 20 mM acetic acid (Merck, Darmstadt, Germany) to a final concentration of 0.05 µg trypsin per µl and stored in aliquots at −80° C. until use. To each of the neutralized IgG samples 8 µl of the trypsin stock (400 µg in total) and 12 µl of water were added. The samples were shaken for 3 min and incubated overnight at 37° C. Tryptic IgG digests were stored at −20° C. until HILIC SPE microtip desalting and purification.

1 mg of fetuin (Sigma-Aldrich) was dissolved in 200 µl 50 mM ammonium bicarbonate containing 10 mM Dithiothreitol (DTT) and reduced at 60° C. for 40 minutes. Cysteine alkylation was achieved by 30 µl 100 mM iodoacetamide dissolved in 50 mM ammonium bicarbonate followed by 30 minutes incubation at room temperature in the dark. The alkylation reaction was stopped by putting the sample under a fluorescent lamp (gas discharge lamp) for 30 minutes. Trypsin digestion was achieved overnight at 37° C. with 20 µg sequencing grade modified trypsin (Promega, Madison, Wis.).

N-Glycan Release

N-glycans from protein A purified IgGs were released (as described Ruhaak et al., *Anal. Chem.* 2008, 80, 6119-6126). Briefly, the dried IgG samples were denatured with 2 µl sodium dodecyl sulfate (SDS) (2%) at 60° C. for 10 min. Subsequently, 2 µl of a release mixture containing 2% Tergitol-type NP-40 (NP-40), 2.5×PBS and 0.05 mU PNGase F (Roche, Mannheim, Germany) was applied. The samples were incubated overnight at 37° C. for N-glycan release.

Human apo-transferrin (0.1 mg; Sigma-Aldrich) was dissolved in 21 µl 50 mM ammonium bicarbonate containing 10 mM DTT and reduced at 60° C. for 40 min. Cysteine alkylation was achieved by 4 µl 200 mM iodoacetamide dissolved in 50 mM ammonium bicarbonate followed by 30 min incubation at room temperature in the dark. The alkylation was stopped by putting the sample under a fluorescent lamp (gas discharge lamp) for 30 min. To the sample, 6 mU PNGase F was applied and incubated overnight at 37° C. for N-glycan release.

Preparing Cotton HILIC SPE Microtips

Cotton wool pads of three different brands (Da, Dynaretail, Leusden, The Netherlands; Etos, Etos bv, Beverwijk, the Netherlands; Bella, Groupe Lemoine; Paris, France) were purchased in local stores and used for the preparation of HILIC SPE microtips. According to the manufacturers the cotton wool pads were made from 100% pure cotton. A small piece of cotton wool with an average weight of 500 µg was taken from a cotton wool pad and pushed into the end part of a 10 µl pipette tip (Rainin, Tiel, The Netherlands) using a blunt needle. Microtips were stored in a closed box until use.

Cotton HILIC SPE of N-Glycans and Tryptic IgG Glycopeptides

The cotton HILIC SPE microtip was washed with 5 times 10 µl of water and conditioned with 3 times 83% of acetonitrile (Biosolve BV, Valkenswaard, The Netherlands) by aspirating and dispensing the solution. For less then 10% of the prepared tips the flow upon solvent aspiration was found to be slow and insufficient, and such tips were therefore discarded. For sample application to the cotton HILIC SPE microtip, 39 µl of acetonitrile was added to 8 µl of a tryptic IgG digest or an N-glycan release sample, and the mixture was pipetted up and down 20 times to allow glycopeptide adsorption. The adsorbed glycans or glycopeptides were washed 3 times with 10 µl of 83% acetonitrile containing 0.1% TFA and eluted directly onto a MALDI plate with 2 µl of water.

MALDI-TOF-MS

For IgG Fc N-glycopeptide profiling by MALDI-TOF-MS in the reflectron positive mode, glycopeptides were directly eluted from cotton HILIC SPE microtips onto a polished stainless steel MALDI plate (Bruker Daltonics, Bremen, Germany) using 2 µl of water and allowed to air dry. Samples were overlaid with 2 µL α-cyano-4-hydroxycinnamic acid (CHCA, 5 mg/ml 50% acetonitrile; Bruker Daltonics) and allowed to air dry.

For glycosylation profiling in the linear positive mode, IgG glycopeptides were directly eluted onto an AnchorChip 600/384 MALDI plate (Bruker Daltonics) and allowed to air dry. Samples were overlaid with 1 µL dihydroxybenzoic acid (DHB, 5 mg/ml 50% acetonitrile with 0.1% TFA; Bruker Daltonics). The AnchorChip plate was covered with a pierced cap containing 5 holes of approximately 5 mm (i.d.), allowing the DHB matrix to air dry at room temperature in a controlled manner.

Samples were analyzed on an Ultraflex II MALDI-TOF/TOF-MS (Bruker Daltonics), and mass spectra were processed with flexAnalysis software (Bruker Daltonics). Similarly, glycans were eluted from cotton HILIC micro-SPEs directly onto an AnchorChip MALDI plate, allowed to air dry, and were overlaid with 1 µL DHB.

Results

IgG Purification and Tryptic Cleavage

IgGs were affinity-captured from 2 µl of human plasma (approximately 20 µg IgG) in 96-well filter plates containing 5 µl of Protein A-Sepharose beads, followed by the elution of IgGs with 40 µl of 100 mM formic acid. While a previously described version of the protocol involves drying of the sample by vacuum centrifugation (Wuhrer et al., Proteomics 2007, 7, 4070-4081), this procedure was replaced by a neutralization step with ammonium bicarbonate in the current protocol.

Tryptic cleavage of IgGs was performed by an overnight incubation at 37° C. either with 200 µg sequencing grade modified trypsin or 400 µg TPCK-treated trypsin. IgG glycopeptides were purified by Sepharose HILIC SPE in 96-well plate format and analyzed by MALDI-TOF-MS in the reflectron-positive mode. The IgG Fc N-glycopeptide profiles obtained for the neutralization procedure were very similar to those observed with the previously described vacuum centrifugation procedure independent of the trypsin used (data not shown).

Glycopeptide Purification Using Cotton HILIC SPE Microtips

Cotton was evaluated for its potential as a stationary phase in HILIC SPE of IgG glycopeptides. To this end, a small piece of a cotton wool pad (approximately 500 µg) was packed into the end of a pipette tip (FIG. 1). From a cotton wool pad (A), approximately 500 µg is taken (B) and pushed into a 10 µl pipette tip using a blunt metal needle (C). The cotton is pushed down into the end part of the tip (D).

The obtained SPE microtips were tested for HILIC mode enrichment of IgG glycopeptides. Specifically, acetonitrile was added to an aliquot of a tryptic digest of human plasma IgG, and glycopeptides were adsorbed to the HILIC SPE stationary phase. After three washes with 10 µl of 83% acetonitrile containing 0.1% TFA, the retained glycopeptides were eluted directly onto a MALDI plate with 2 µl of water, followed by MALDI-TOF-MS profiling of IgG Fc N-glycopeptides.

Figure 1A:
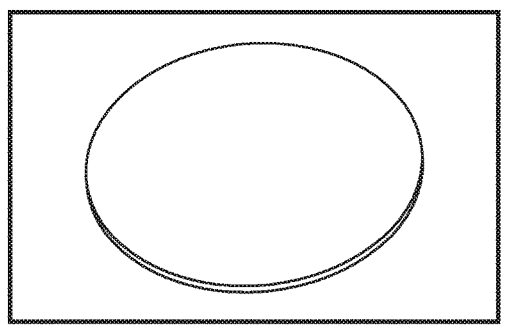
Figure 1B:
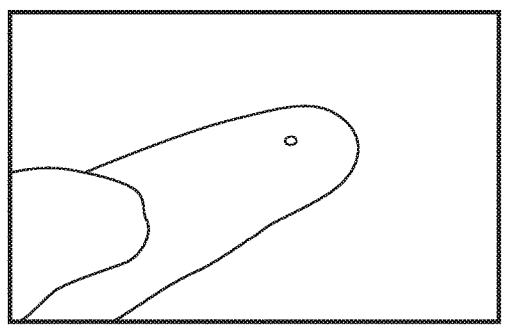
Figure 1C:
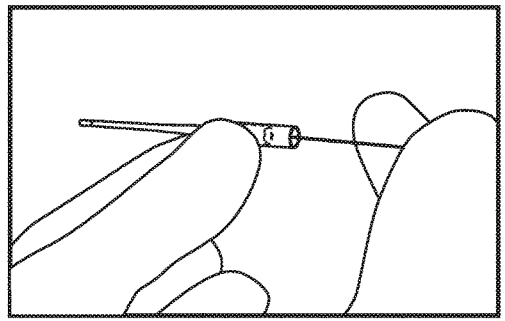
Figure 1D:
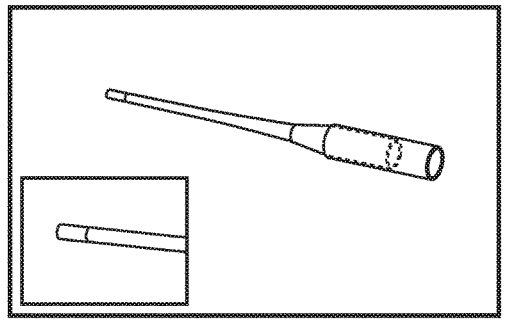
Figure 2A:
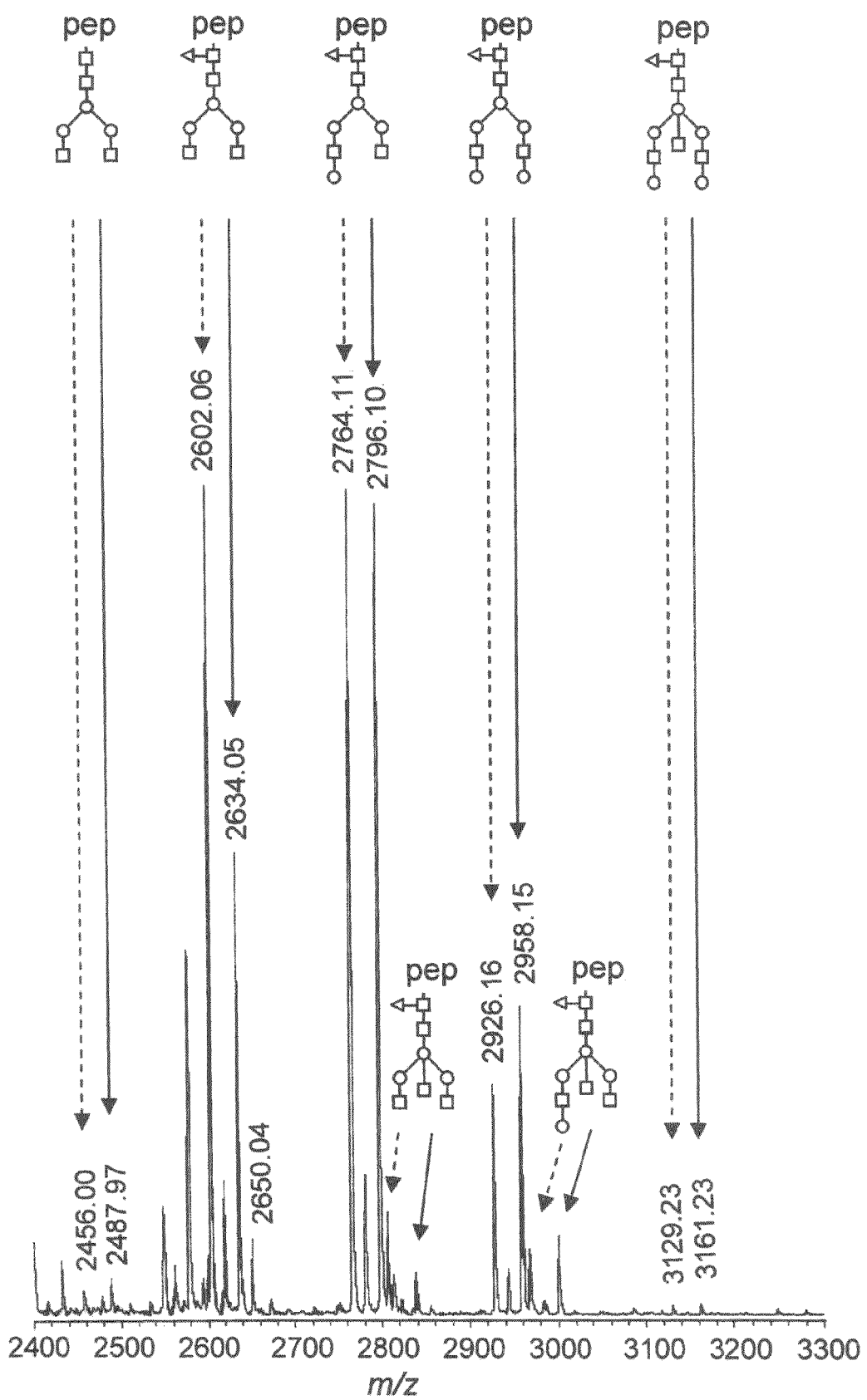
Figure 2B:
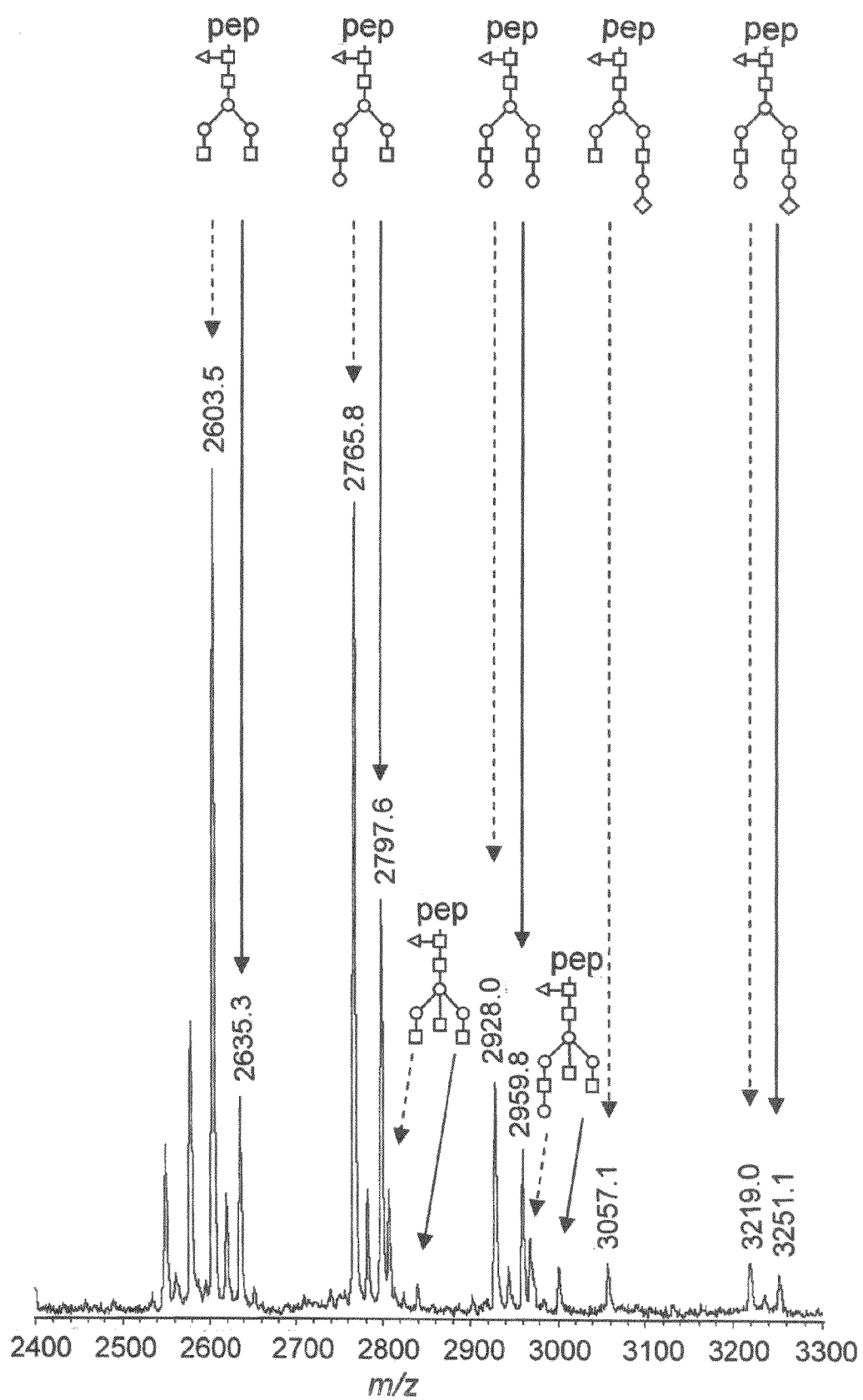

Examples of the glycopeptide profiles registered by reflectron-mode and linear-mode MALDI-TOF-MS are shown in FIG. 2. Obtained IgG1 and IgG2 N-glycosylation profiles were very similar to those obtained previously after 96-well plate sample preparation of IgG glycopeptides using either reverse phase-SPE desalting or Sepharose HILIC SPE purification (FIG. 3).

FIG. 2 shows MALDI-TOF-mass spectrometric profiles of IgG glycopeptides prepared using cotton HILIC SPE microtips. Mass spectra were registered in reflectron-mode using CHCA matrix (A) and in linear-mode using DHB matrix (B). IgG1 and IgG2 glycopeptides are represented by continued and dashed arrows, respectively: square, N-acetylglucosamine; triangle, fucose; dark circle, mannose; light circle, galactose; diamond, N-acetylneuraminic acid; pep, peptide moiety.

MALDI-TOF-MS profiles obtained from blank elutions using cotton HILIC SPE microtips were found to be virtually identical to MALDI matrix controls (only Matrix, no sample spotted), and no cotton wool-related contaminant peaks were detected in the MALDI-TOF-MS profiles (data not shown).

Validation of Cotton HILIC SPE

Figure 4A:
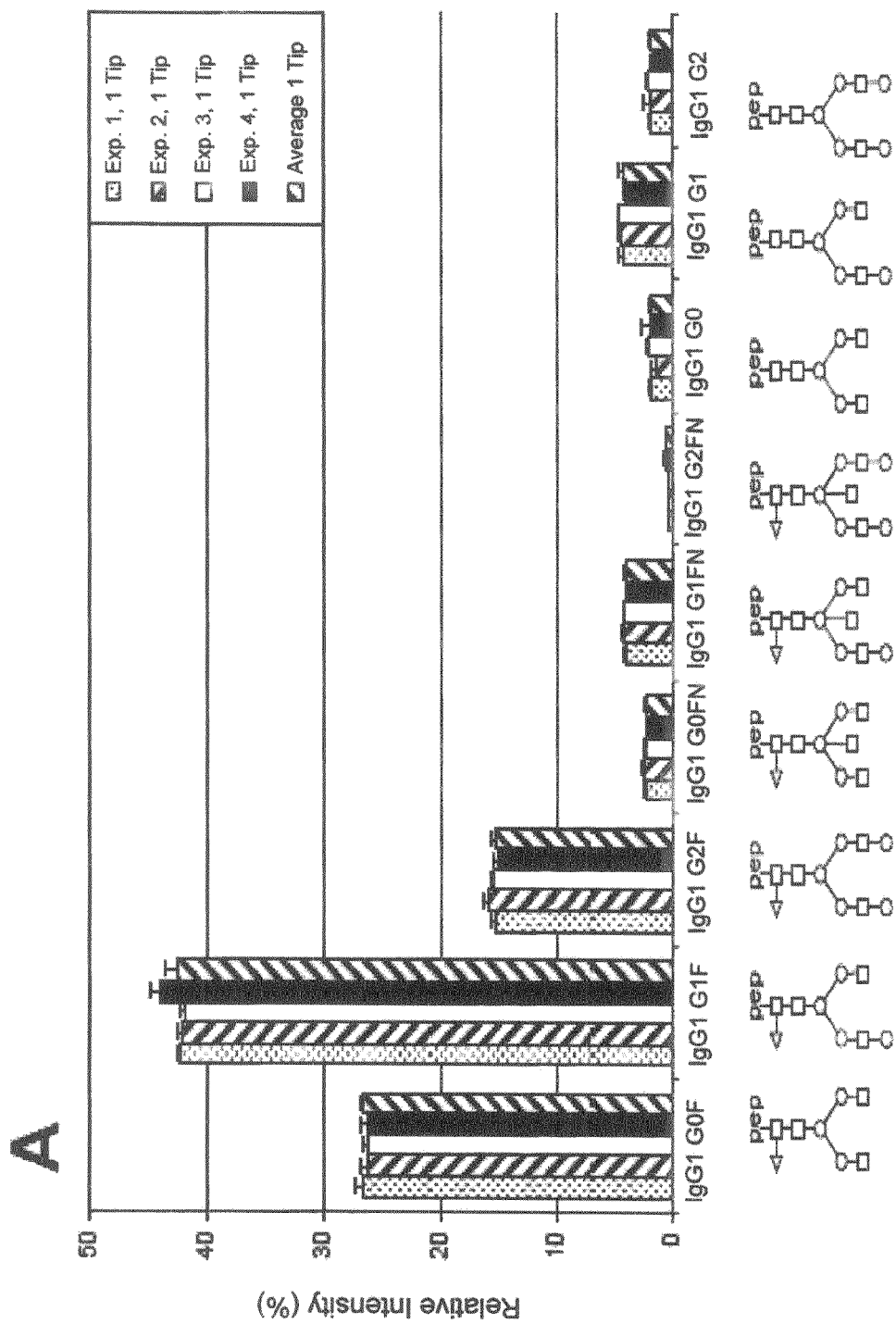
Figure 4B:
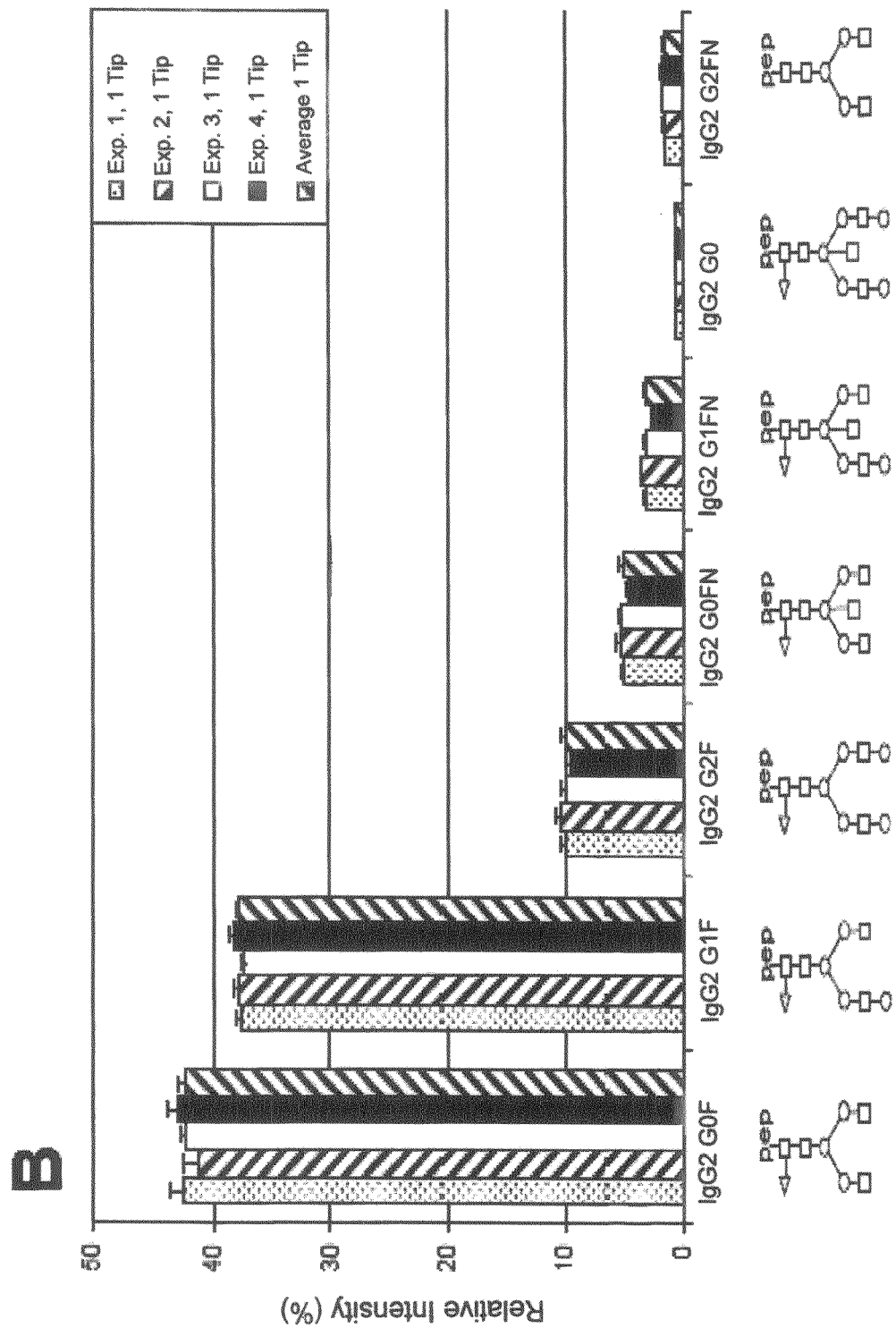

One cotton HILIC SPE microtip was used 8 times for glycopeptide purification from a tryptic IgG digest pool followed by reflectron-mode MALDI-TOF-MS of the eluted glycopeptides (as shown in FIGS. 4A and 4B).

Figure 4C:
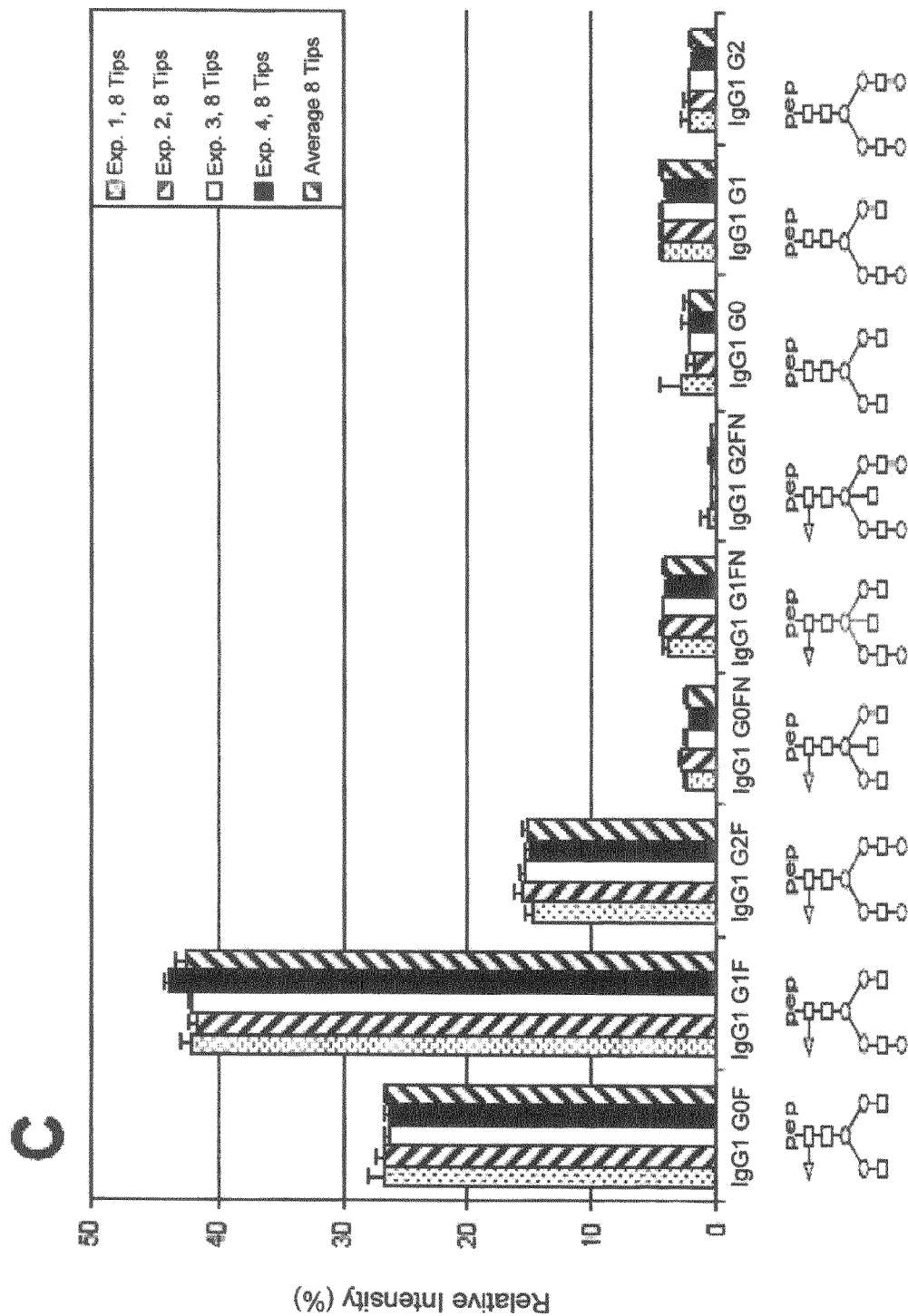
Figure 4D:
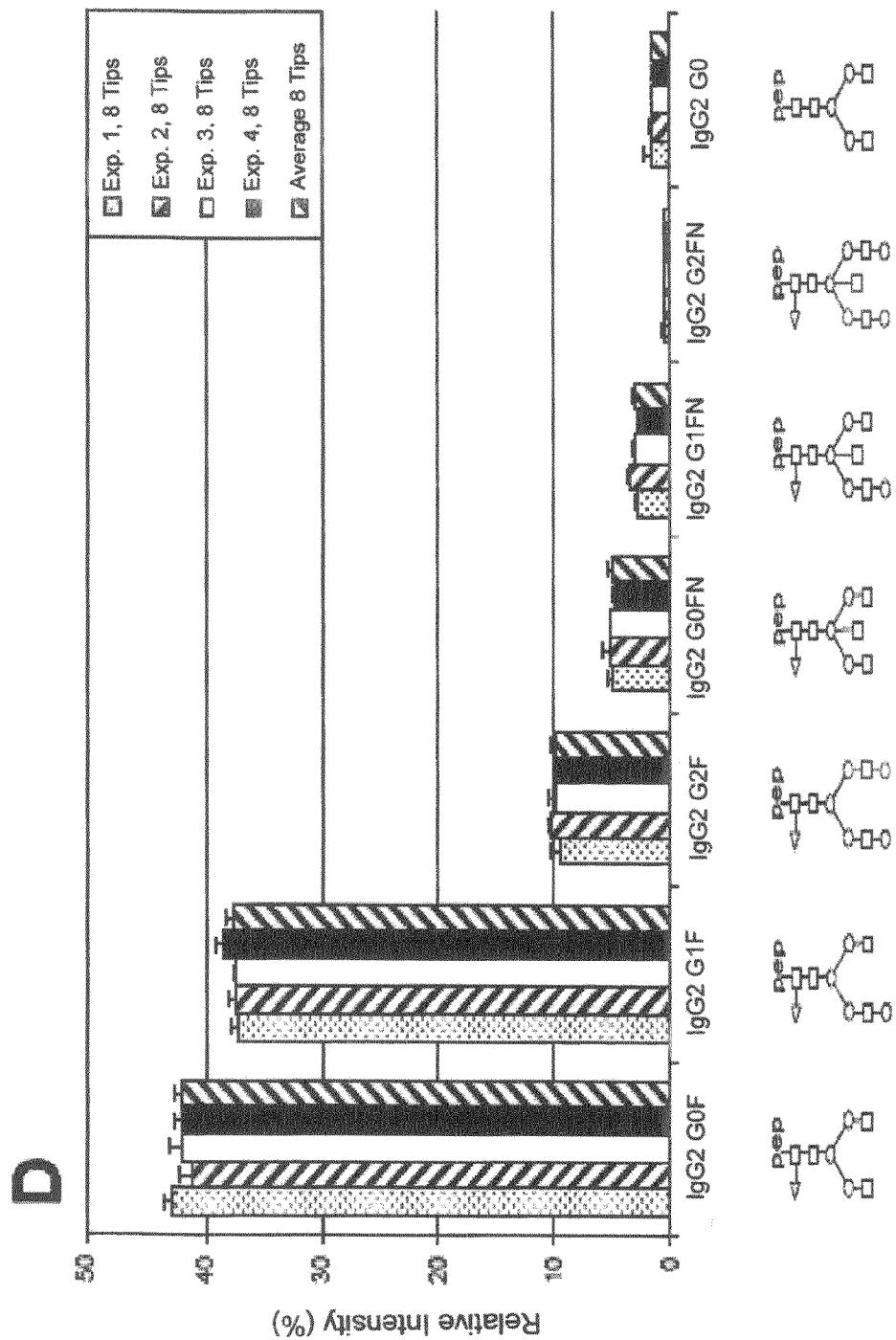
Figure 5A:
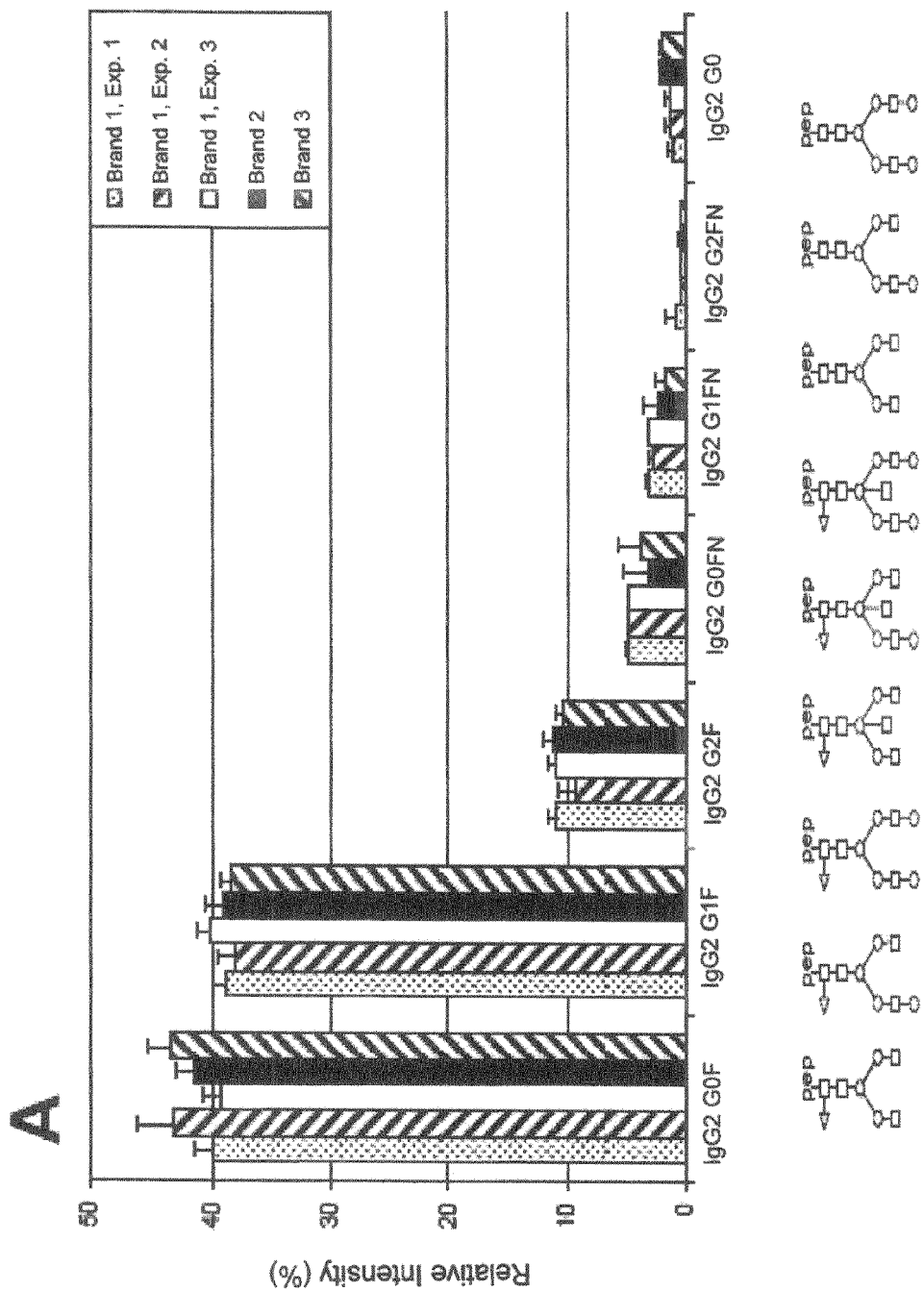
Figure 5B:
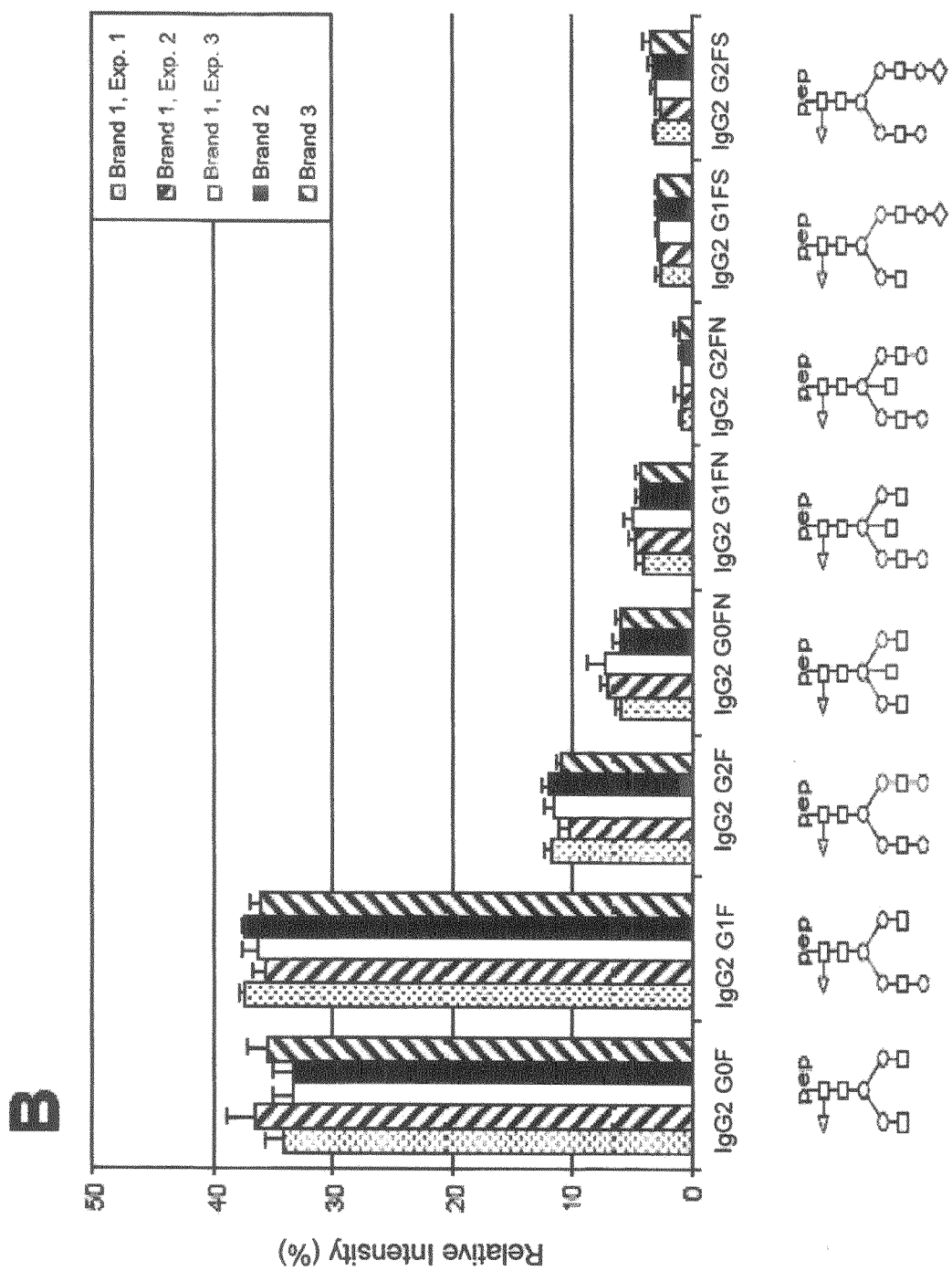
Figure 5C:
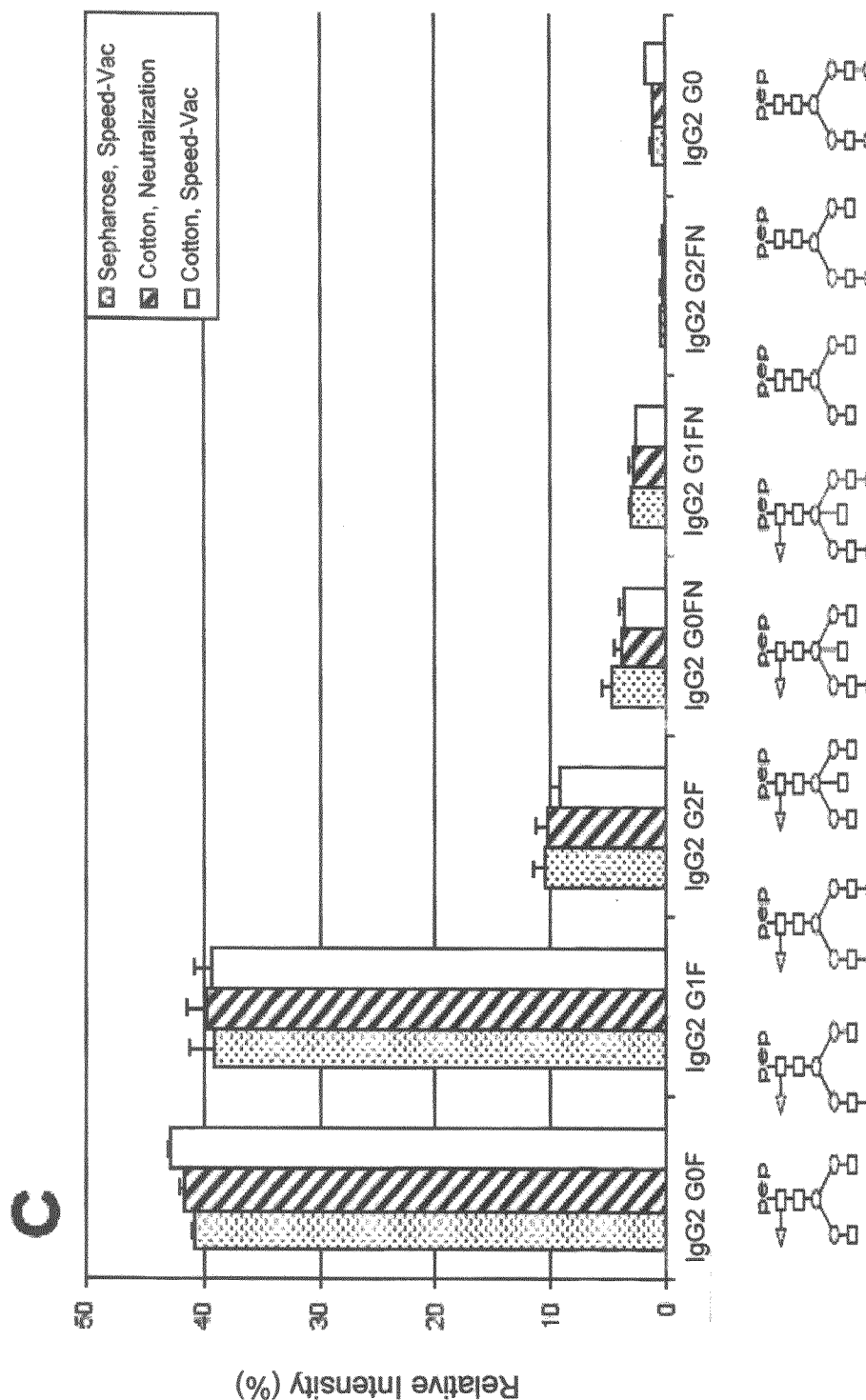
Figure 5D:
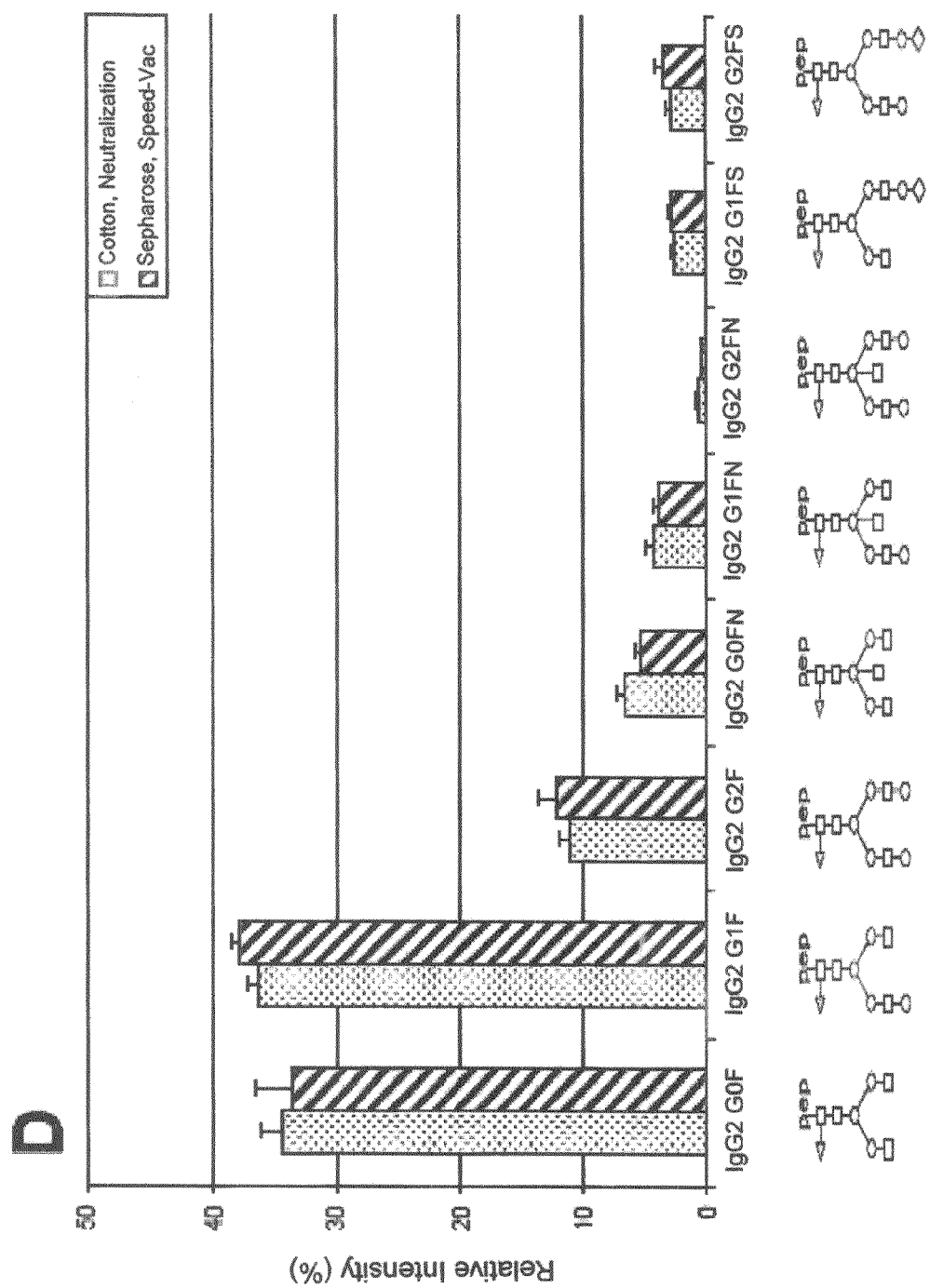
Figure 6A:
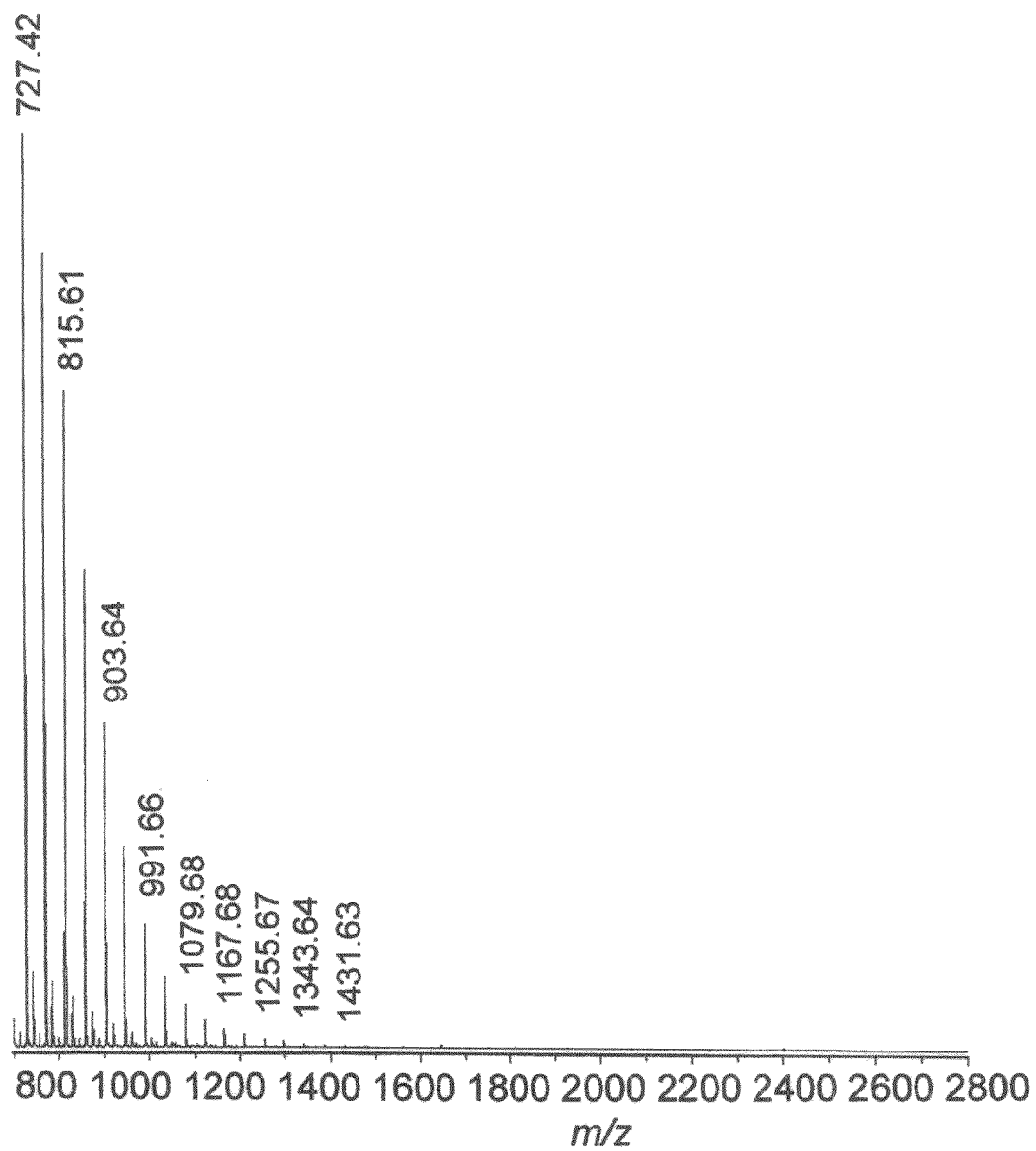
FIG. 6 shows RP-MALDI-TOF-MS of released N-glycans from Protein A captured IgG prior to cotton HILIC (A) and after cotton HILIC purification (B)
Figure 6B:
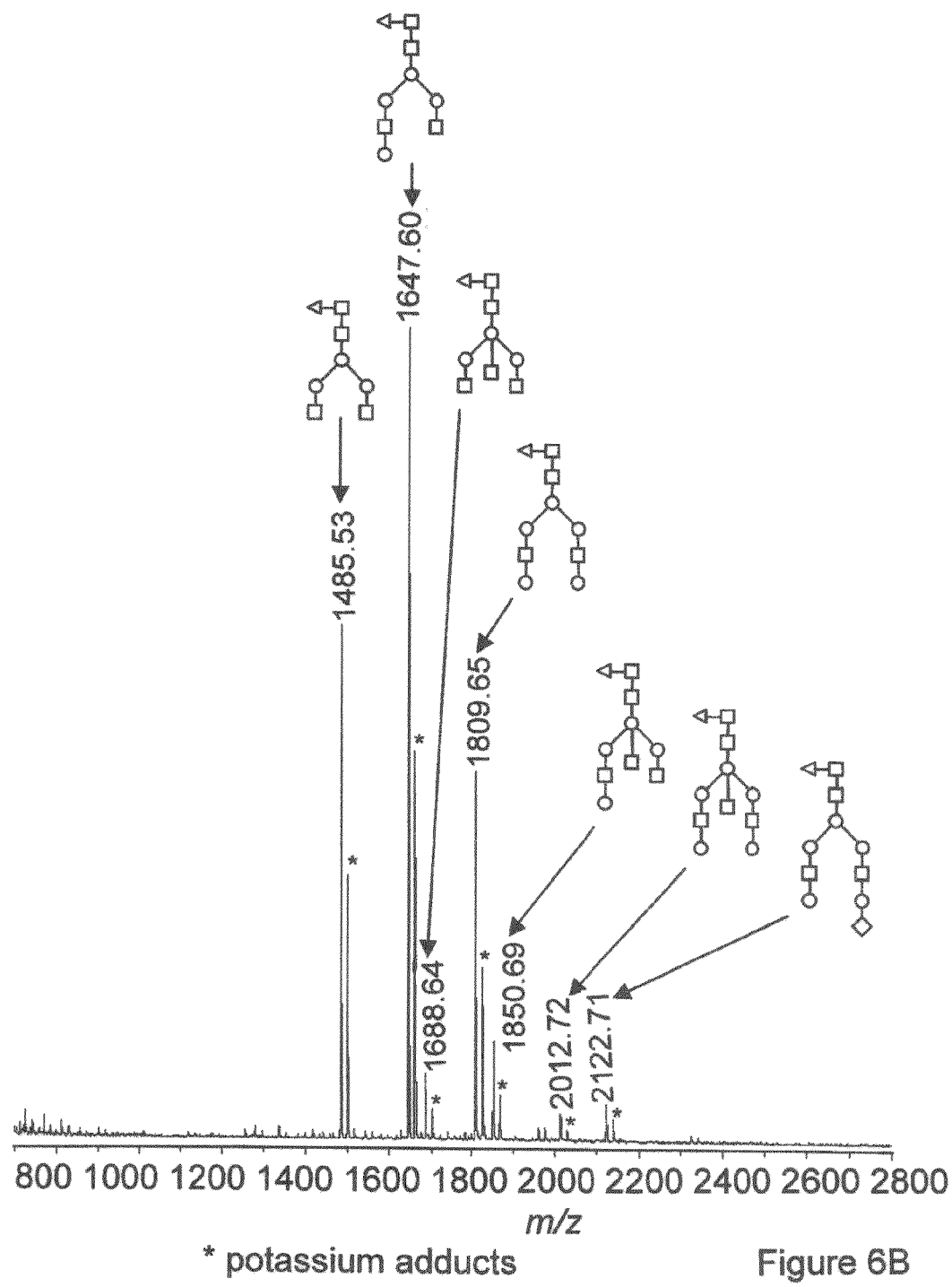
Figure 7A:
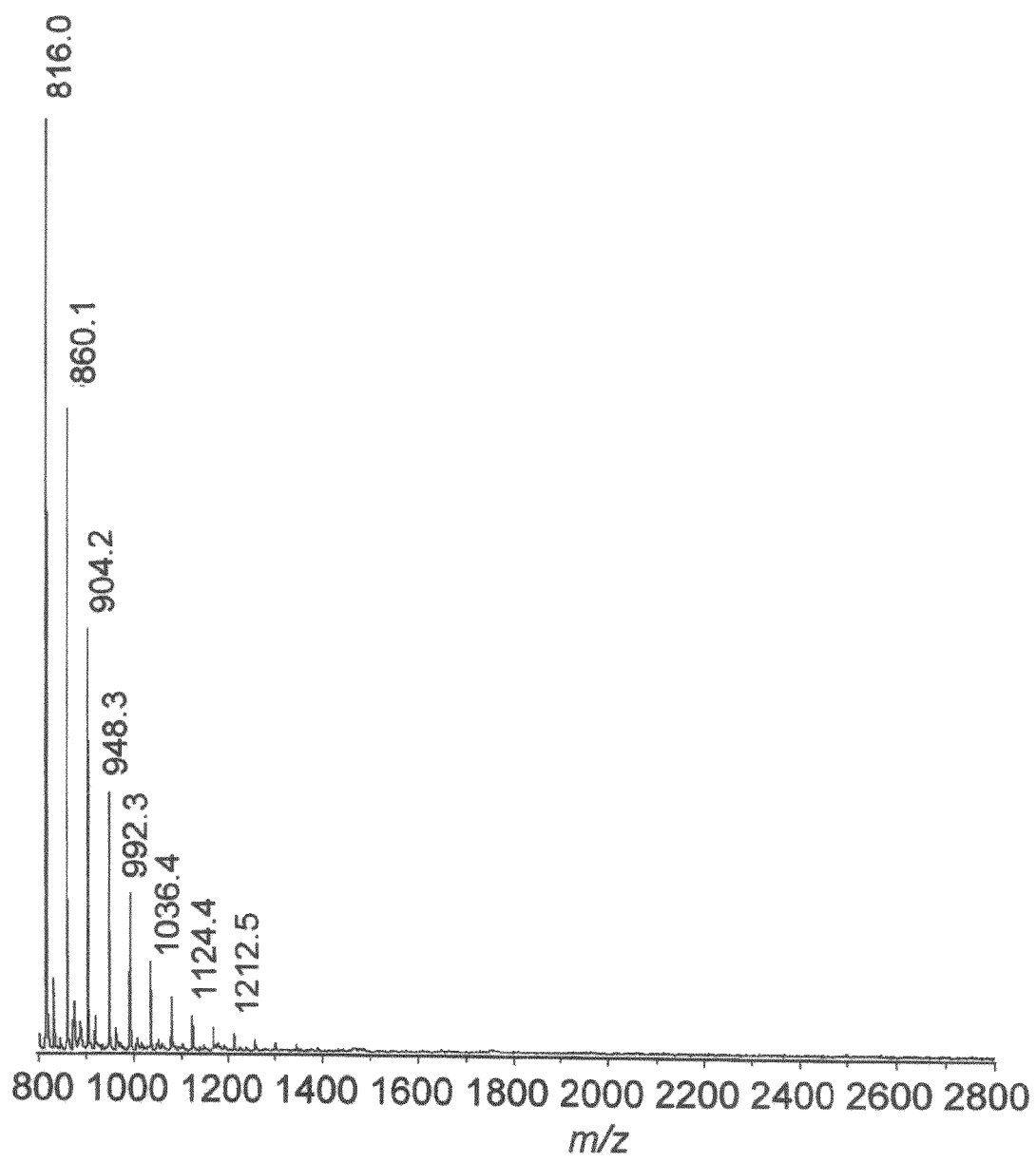
FIG. 7 shows LP-MALDI-TOF-MS of released N-glycans from Protein A captured IgG prior to cotton HILIC (A) and after cotton HILIC purification (B)
Figure 7B:
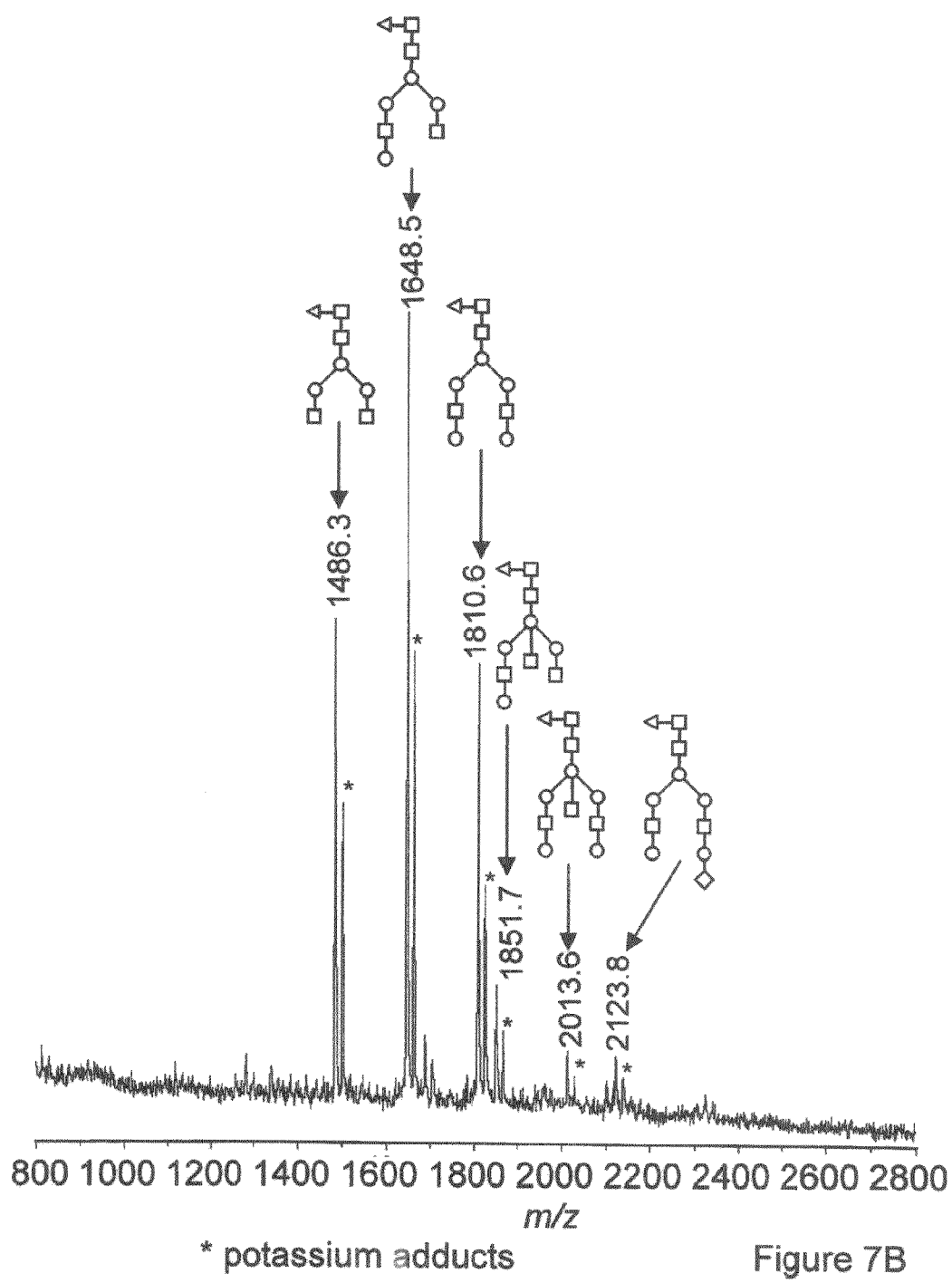
Figure 8A:
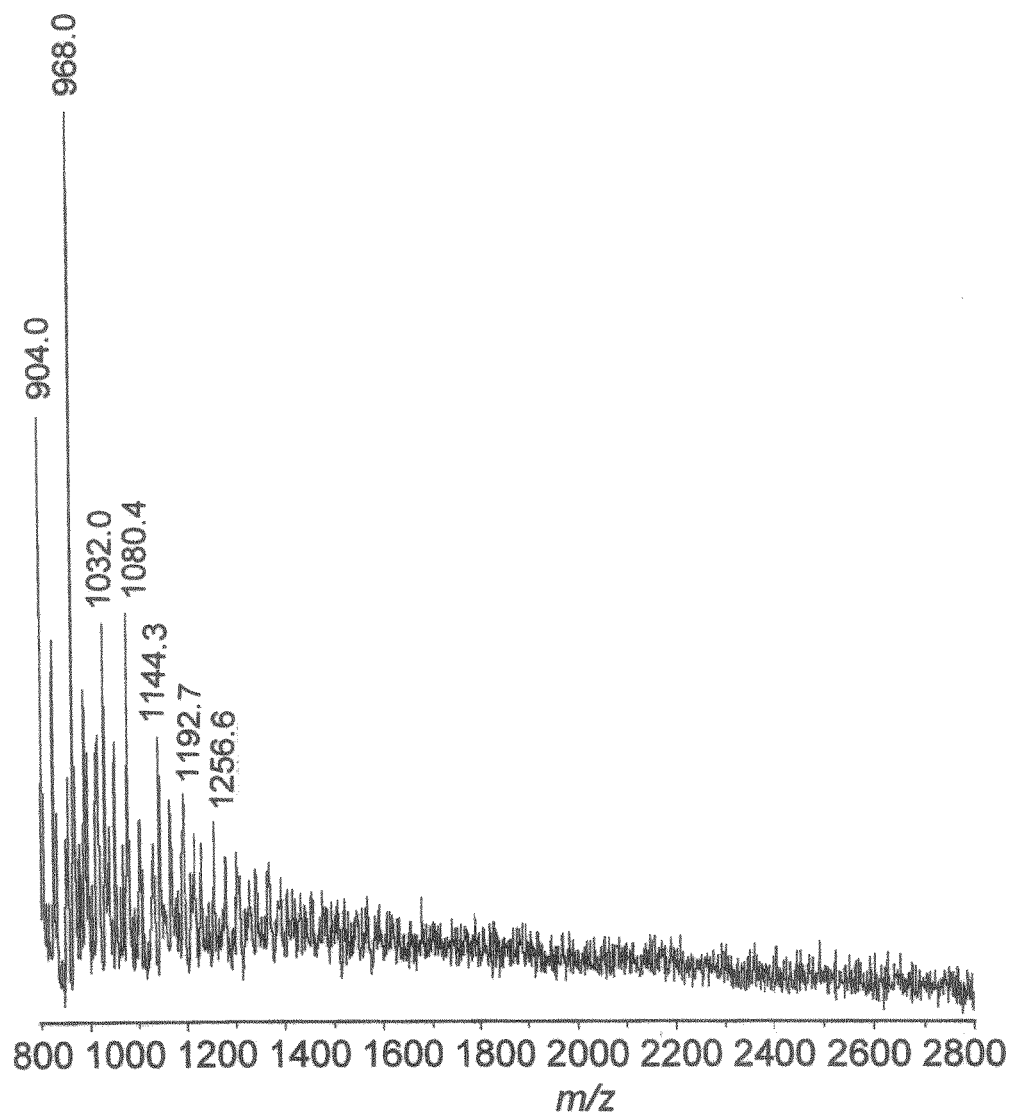
FIG. 8 shows linear negative mode-MALDI-TOF-MS of released N-glycans from Protein A captured IgG prior to cotton HILIC (A) and after cotton HILIC purification (B)
Figure 8B:
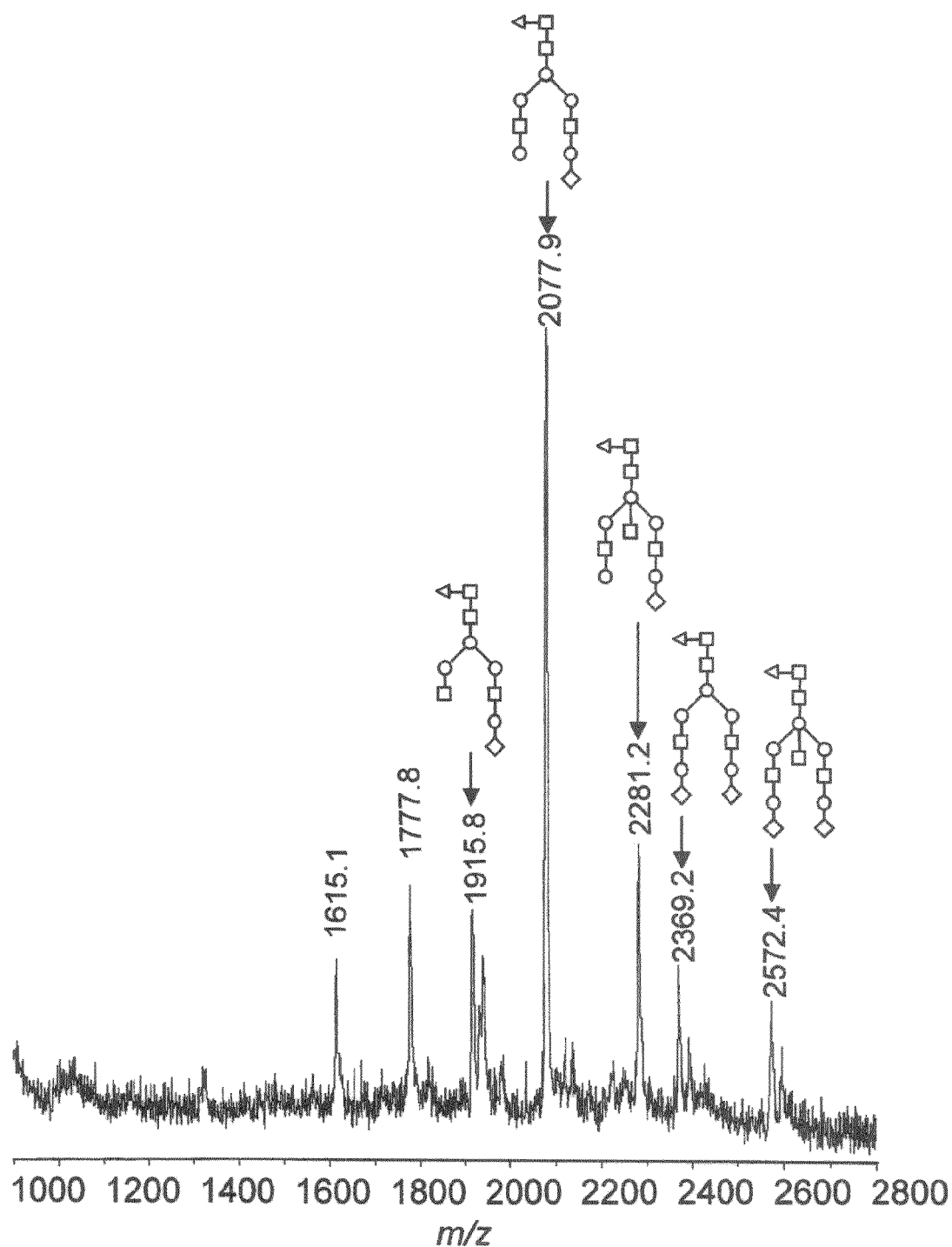
Figure 9A:
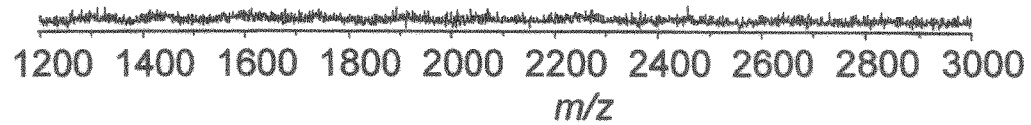
FIG. 9 shows linear negative mode-MALDI-TOF-MS of released N-glycans from transferrin prior to cotton HILIC (A) and after cotton (B)
Figure 9B:
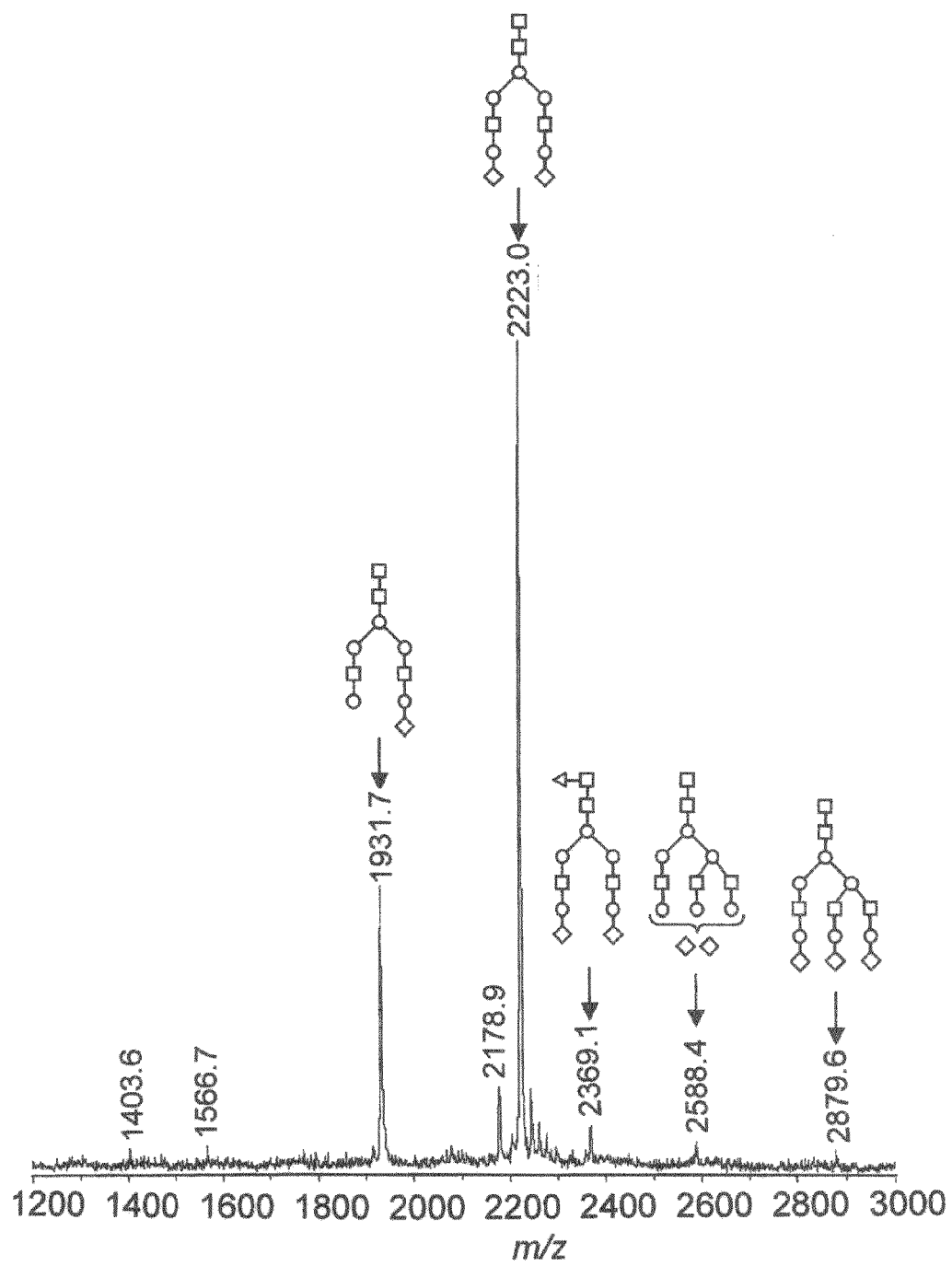

This experiment was repeated on four different days using a new cotton HILIC SPE tip for each experiment. In another set of experiments, 8 different tips were used for IgG Fc N-glycosylation profiling from the above-mentioned tryptic IgG digest pool (as shown in FIGS. 4C and 4D). This experiment was also repeated on four different days using new tips for each experiment. Highly reproducible IgG Fc N-glycosylation profiles were obtained after cotton HILIC SPE, independent of using the same tip repeatedly or using different tips for micro-scale purification and enrichment.

FIG. 4 shows the repeatability of cotton HILIC SPE microtips for desalting and purification of IgG glycopeptides. Analysis was performed by reflectron-mode MALDI-TOF-MS with CHCA matrix. A tryptic IgG digest pool was desalted 8 times either with one cotton HILIC microtip (A and B) or with eight different cotton HILIC microtips (C and D). The experiment was repeated on four different days.

Validation of the Complete Method

Figure 3A:
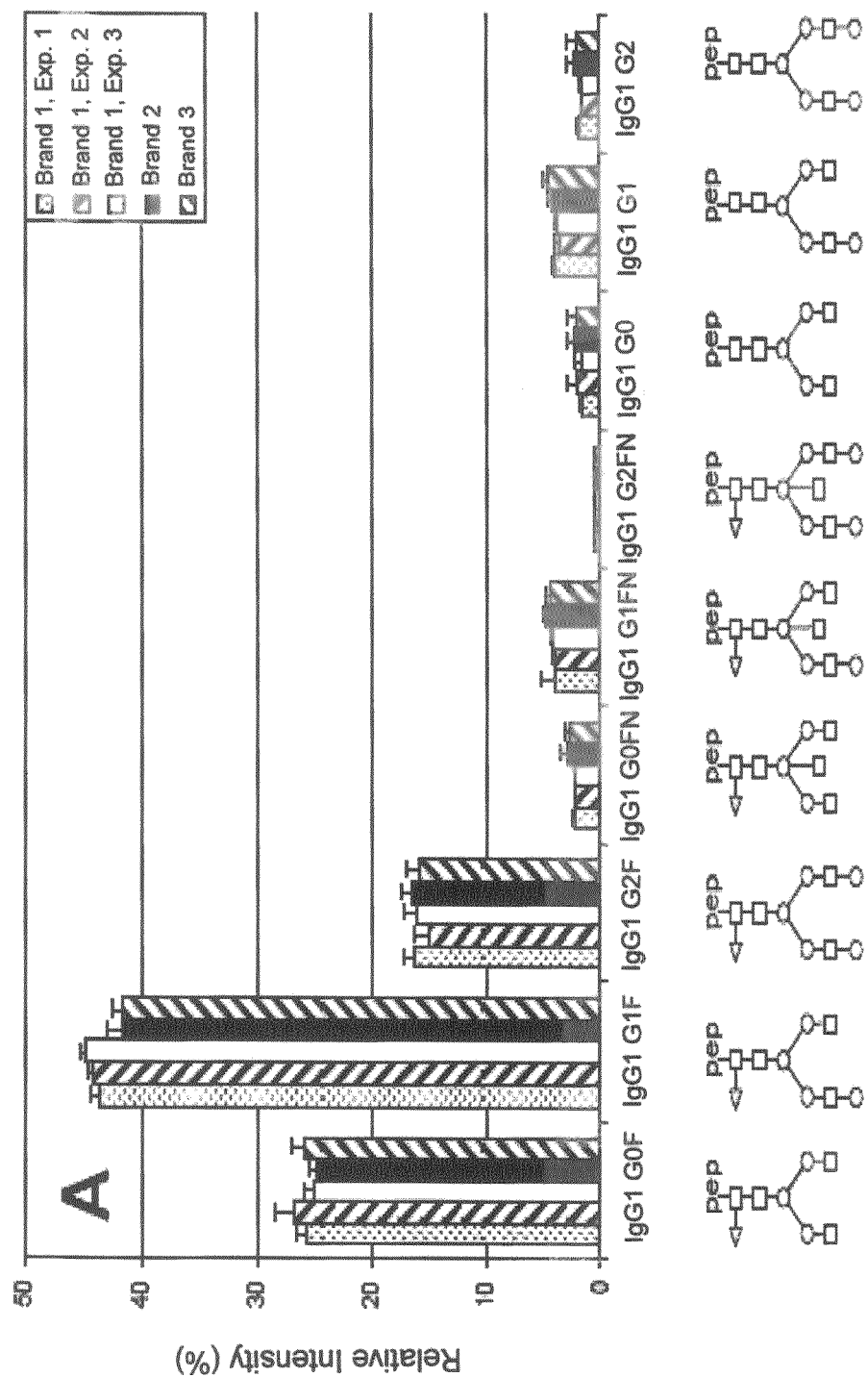
Figure 3B:
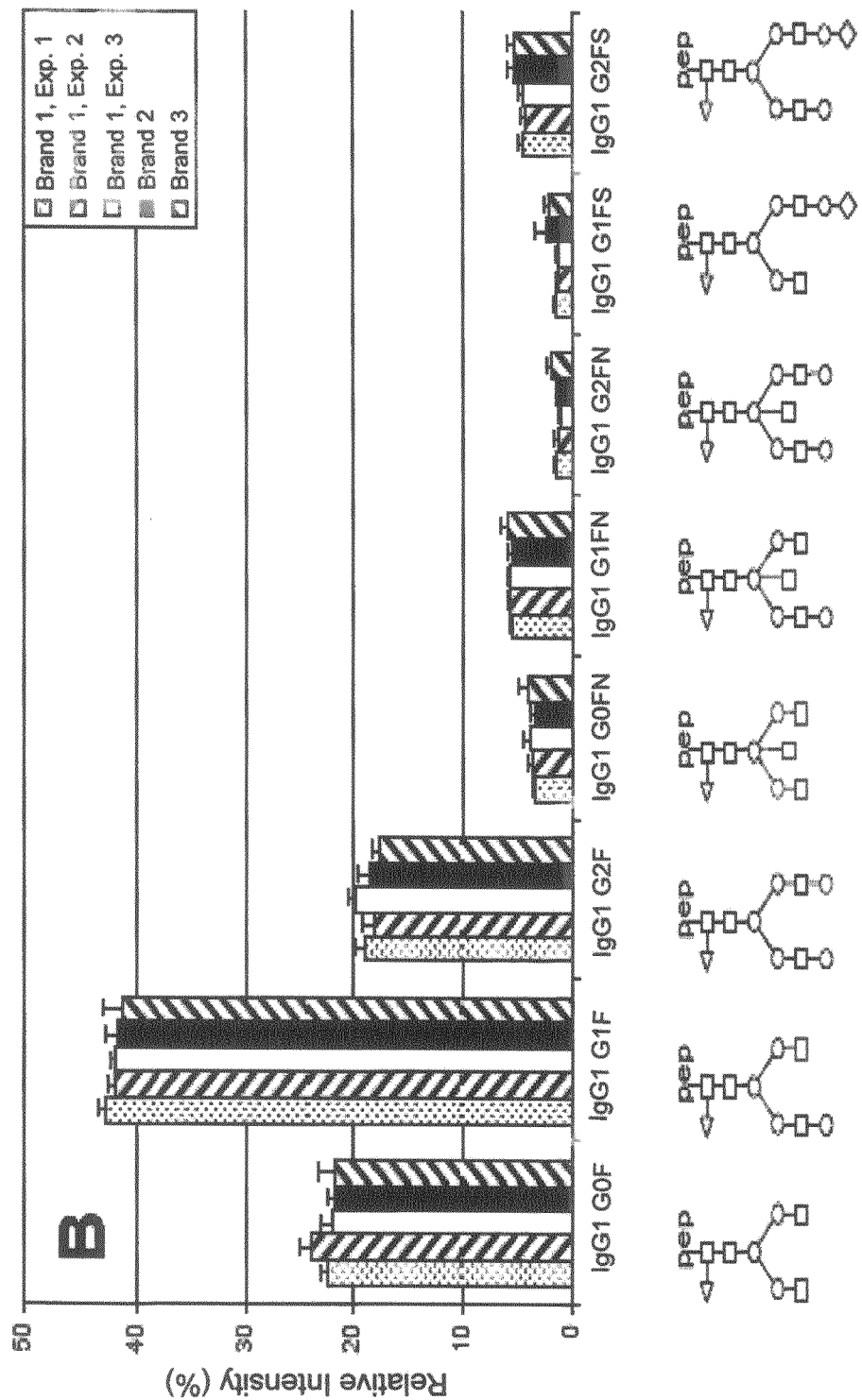
Figure 3C:
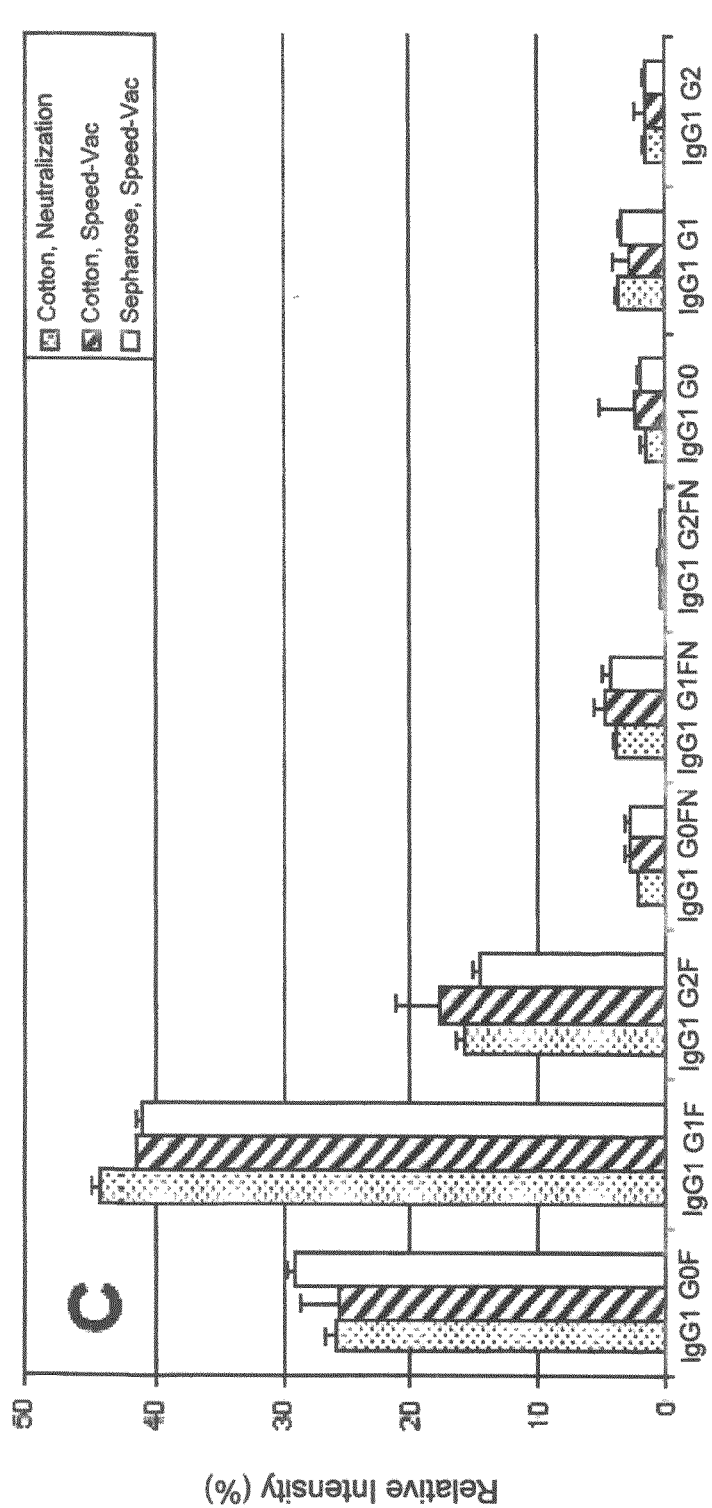
Figure 3D:
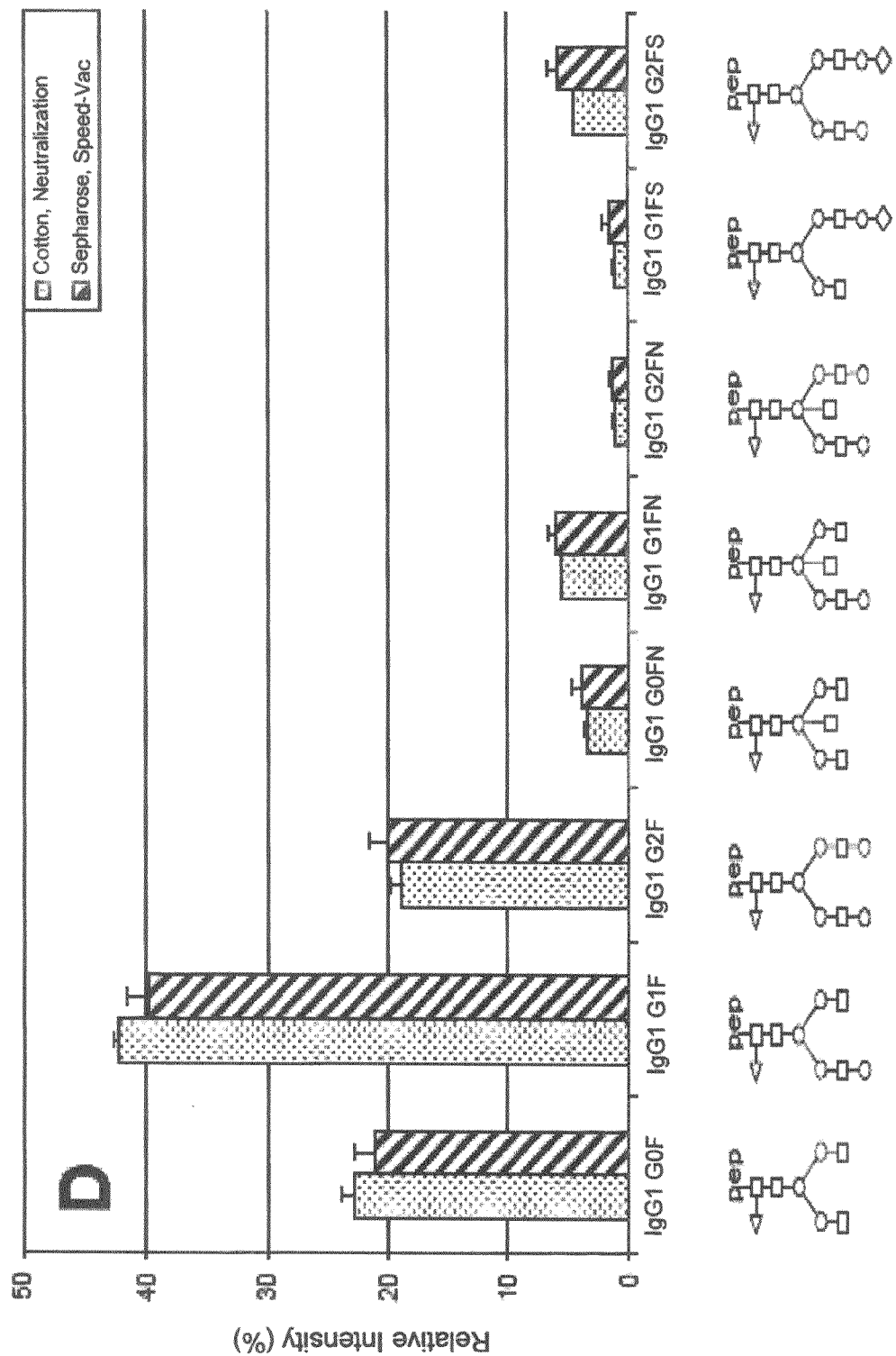

IgG Fc N-glycosylation profiling was performed in parallel on eight plasma aliquots of a control individual. This involved Protein A capturing, neutralization of the eluate, cleavage using TPCK-trypsin, cotton HILIC SPE, and MALDI-TOF-MS analysis. This procedure was repeated on three different days. Mass spectrometric analyses were performed in reflectron mode and linear mode, demonstrating that both IgG1 (as shown in FIGS. 3A and 3B) and IgG2 (as shown in FIGS. 5A, 5B, 6A and 6B) Fc N-glycosylation profiles could be registered with low intraday and interday variability.

Next to the above mentioned cotton material, two other brands of cotton wool pads were used for HILIC SPE microtip preparation and IgG Fc N-glycosylation profiling. All three brands of cotton wool pads provided very similar results for both IgG1 (FIGS. 3A and 3B) and IgG2 (as shown in FIGS. 5A, 5B, 6A and 6B).

Moreover, the method was compared to a previously described approach by Selman et al *Anal. Chem.* 2010, 82, 1073-1081. The major differences compared to this previous method are that (1) drying of Protein A eluates by vacuum centrifugation was replaced for a neutralization step, (2) sequencing grade trypsin was replaced by TPCK-treated trypsin, and (3) cotton HILIC microtip SPE was performed instead of 96-well plate HILIC SPE using Sepharose beads.

A third approach combined the previously described sample preparation by Selman et al (i.e. protein A capturing, drying by vacuum centrifugation, and digestion of IgG with sequencing grade trypsin) with cotton HILIC SPE purification and reflectron mode MALDI-TOF-MS analysis. With all different protocols, very similar IgG1 (FIGS. 3C and 3D) and IgG2 (as shown in FIGS. 5A, 5B, 7A and 7B) Fc N-glycosylation profiles were obtained by reflectron mode and linear mode MALDI-TOF-MS.

FIG. 3 shows the repeatability of IgG1 glycopeptide profiling applying cotton HILIC SPE microtips. IgG1 glycopeptides were detected by MALDI-TOF-MS in reflectron-mode using CHCA matrix (A, C) and in linear-mode using DHB matrix (B, D). Samples were prepared after digestion using the neutralization method followed by desalting with cotton HILIC SPE microtips prepared from three different brands of cotton wool pads (A, B).

FIG. 5 shows the repeatability of IgG2 glycopeptide profiling applying cotton HILIC SPE microtips. IgG2 glycopeptides were detected by MALDI-TOF-MS in reflectron-mode using CHCA matrix (A, C) and in linear-mode using DHB matrix (B, D). Samples were prepared after digestion using the neutralization method followed by desalting with cotton HILIC SPE microtips prepared from three different brands of cotton wool pads (A, B). The resulting profiles were compared with the pattern of glycoforms purified by Sepharose beads or cotton HILIC SPE microtips after drying by vacuum centrifugation, and digestion with sequencing grade trypsin (C, D). For each independent experiment, relative intensities and RSDs were calculated from 8 replicates.

The resulting profiles were compared with the pattern of glycoforms purified by Sepharose beads or cotton HILIC SPE microtips after drying by vacuum centrifugation, and digestion with sequencing grade trypsin (C, D). For each independent experiment, relative intensities and RSDs were calculated from 8 replicates.

Glycan Purification Using Cotton HILIC SPE Microtips

As another field of application cotton HILIC SPE microtips were tested for the MALDI-TOF-MS sample preparation of glycans after PNGase F release. N-glycans were enzymatically released from human IgG and human transferrin samples containing detergents (SDS, NP-40) and salt (PBS). Both neutral and acidic (sialylated) N-glycans were detected by MALDI-TOF-MS after cotton HILIC micro-SPE purification whilst direct MALDI-TOF-MS analysis of the glycan release samples without SPE purification did not allow registration of N-glycans but was dominated by detergent clusters (FIGS. 6, 7, 8 and 9).

FIGS. 6, 7, 8 and 9 show spectra from MALDI-TOF-MS of N-glycans after cotton HILIC micro-SPE purification. N-glycans enzymatically released from IgG (FIGS. 6, 7 and 8, spectra A-F) and human transferrin (FIG. 9, spectra G, H) were analyzed by MALDI-TOF-MS in the reflectron positive mode (FIG. 6, spectra A, B), linear positive mode (FIG. 7, spectra C, D), and linear negative mode (FIGS. 8 and 9, spectra E-H) without (left panels: spectra A, C, E, G) and with (right panels: spectra B, D, F, H) prior purification by cotton HILIC micro-SPE. Glycans were registered as sodium adducts in positive-ion mode and as deprotonated species in negative-ion mode:*, potassium adduct; square, N-acetylglucosamine; triangle, fucose; dark circle, mannose; light circle, galactose; purple diamond, N-acetylneuraminic acid.

Figure 10:
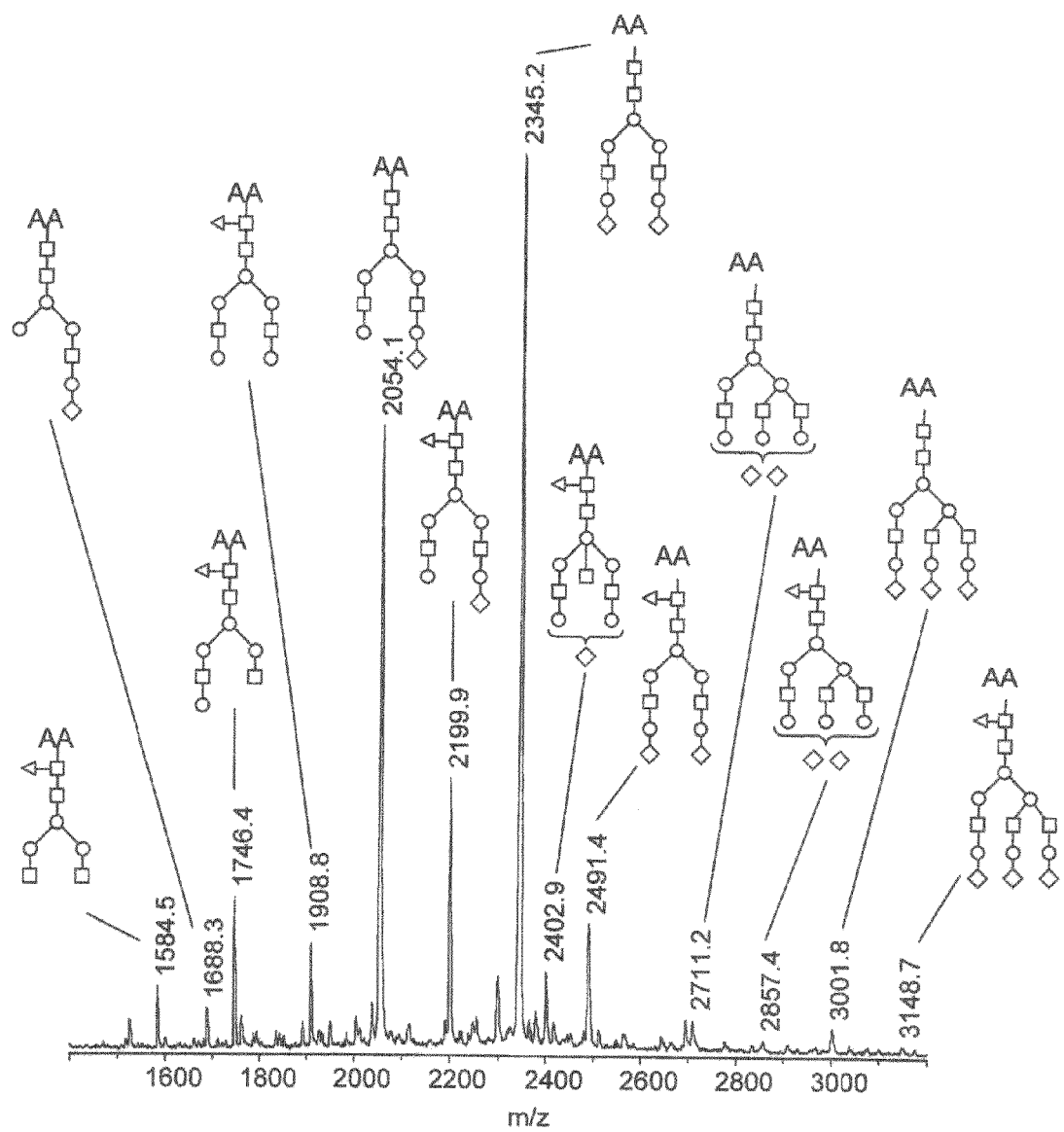
FIG. 10 shows a linear-negative ion mode MALDI-TOF-MS spectrum of PNGase F released N-glycans from human plasma proteins labeled with 2-aminobenzoic acid (AA) by reductive amination and thereafter purified using cotton HILIC SPE microtips.

FIG. 10 shows a linear-negative ion mode MALDI-TOF-MS spectrum of PNGase F released N-glycans from human plasma proteins labeled with AA. N-glycans were released from human plasma proteins (2 µl plasma) with PNGase F as described previously (Ruhaak et al, 2008, Anal Chem., 80, 6119-6126), purified by cotton HILIC micro-SPE, and measured on an AnchorChip target plate with DHB; square, N-acetylglucosamine; triangle, fucose; dark circle, mannose; light circle, galactose; diamond, N-acetylneuraminic acid; *, post source decay products.

FIG. 11 (spectra A and B) show linear-negative ion mode MALDI-TOF-MS spectra of tryptic glycopeptides (A) and PNGase F released N-glycans (B) from bovine fetuin (SwissProt entry number: P12763). Glycopeptides and glycans were purified by cotton HILIC micro-SPE and measured on an AnchorChip target plate with DHB. (A) Solid arrows, small molecular mass glycopeptide (L145CPDCPLLAPLNDSR159); dashed arrows, intermediate molecular mass glycopeptide (V160VHAVEVALATFNAESNGSYLQLVEISR187); dotted arrows, large molecular mass glycopeptide (R72PTGEVYDIEIDTLETTCHVLDPTPL ANCSVR103); (B) ~, Fetuin peptide H313TFSGVASVESSSGEAFHVG K333; *, sodium adduct; ¥, potassium adduct; square, N-acetylglucosamine; triangle, fucose; dark circle, mannose; light circle, galactose; diamond, N-acetylneuraminic acid.

FIG. 12 (spectra A and B) shows linear-negative ion mode MALDI-TOF-MS spectra of tryptic glycopeptides (A) and PNGase F released N-glycans (B) from human apo-transferrin glycopeptides (SwissProt entry number: P02787). Glycopeptides and glycans were purified by cotton HILIC micro-SPE and measured on an AnchorChip target plate with DHB. (A) Solid arrows, small molecular mass glycopeptide (C421GLVPVLAENYNK433); dashed arrows, large molecular mass glycopeptide (Q622QQHLFGSNVTDCSGNFCLFR642); ¥, post source decay products; *, ammonia loss by N-terminal peptide degradation during proteolytic digestion (B) *, sodium adduct; ¥, potassium adduct; square, N-acetylglucosamine; triangle, fucose; dark circle, mannose; light circle, galactose; diamond, N-acetylneuraminic acid.

Therefore, these experiments demonstrated the successful clean-up of N-glycan release samples by cotton HILIC SPE for MALDI-TOF-MS analysis with removal of detergents and salts.

The listing or discussion of an apparently prior-published document in this specification should not necessarily be taken as an acknowledgement that the document is part of the state of the art or is common general knowledge.

The invention claimed is:

1. A hydrophilic interaction liquid chromatography solid phase extraction method of purifying a glycan and/or glycoconjugate, the method comprising:
    applying a glycan and/or glycoconjugate-containing sample comprising an organic solvent to a stationary phase that is cotton wool fibers;
    washing the stationary phase with a first solvent which is a solvent mixture comprising between 70% volume per volume (v/v) and 95% v/v organic solvent and between 0.1% v/v to 3% v/v acid in water; and
    eluting the glycan and/or glycoconjugate from the stationary phase with a second solvent, wherein the second solvent is one of water, dimethylsulfoxide, or dimethylformamide.

2. The method of claim 1, wherein the organic solvent of the glycan and/or glycoconjugate-containing sample at least one of acetonitrile, methanol, ethanol, propanol, isopropanol, butanol, or tetrahydrofuran.

3. The method of claim 1, wherein the organic solvent of the first solvent comprises at least one of acetonitrile, methanol, ethanol, propanol, isopropanol, butanol, or tetrahydrofuran, and the acid comprises at least one of trifluoroacetic acid, formic acid, acetic acid, pentafluoropropionic acid, or heptafluorobutyric acid.

4. The method of claim 1, wherein the second solvent comprises more polar solvent than the first solvent.

5. The method of claim 1, wherein the glycoconjugate comprises at least one of a glycoprotein, glycopeptide or glycolipid.

6. The method of claim 1, wherein the glycan comprises a N-glycan.

7. The method of claim 1, wherein the stationary phase is re-usable.

8. The method of claim 1, wherein the stationary phase contains about 500 μg of the cotton wool fibers.

9. The method of claim 1, further comprising performing mass spectrometric analysis on the eluted glycan and/or glycoconjugate.

10. The method of claim 1, further comprising glycosylation profiling at a glycopeptide level of the eluted glycopeptides.

11. The method of claim 1, wherein the stationary phase is held in an open ended vessel.

12. The method of claim 1, wherein the method is utilized to one of extract glycans after PNGase F treatment of glycoproteins, extract glycans after fluorescent labelling by reductive amination, or enrich N-glycopeptides from proteolytic digests.

13. The method of claim 1, including, a kit for purifying a glycan and/or glycoconjugate, the kit comprising:
    a stationary phase that is cotton wool fibers; and
    instructions for purifying a glycan and/or glycoconjugate according to the method of claim 1.

14. The method of claim 2, wherein the organic solvent of the glycan and/or glycoconjugate-containing sample is between 70% and 88% v/v acetonitrile in water.

15. The method of claim 3, wherein the first solvent mixture comprises between 75% and 90% v/v organic solvent and between 0.1% and 1% v/v acid in water.

16. The method of claim 5, wherein the glycopeptide is an IgG glycopeptide.

17. The method of claim 16, wherein the IgG glycopeptide is a tryptic IgG Fc N-glycopeptide.

18. The method of claim 9, wherein the mass spectrometric analysis is MALDI-TOF MS detection.

19. The method of claim 11, wherein the open-ended vessel is one of a pipette, a multi-channel pipette or a pipette tip.

20. The method of claim 11, wherein the open-ended vessel is a microtip.

* * * * *